US009568725B2

(12) United States Patent
Ushio

(10) Patent No.: US 9,568,725 B2
(45) Date of Patent: Feb. 14, 2017

(54) ENDOSCOPE OBJECTIVE OPTICAL SYSTEM

(71) Applicant: OLYMPUS CORPORATION, Hachioji-shi, Tokyo (JP)

(72) Inventor: Yasuaki Ushio, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/195,778

(22) Filed: Jun. 28, 2016

(65) Prior Publication Data

US 2016/0306162 A1 Oct. 20, 2016

Related U.S. Application Data

(63) Continuation of application No. PCT/JP2015/072913, filed on Aug. 13, 2015.

(30) Foreign Application Priority Data

Aug. 28, 2014 (JP) .................................. 2014-174132

(51) Int. Cl.
*G02B 13/04* (2006.01)
*G02B 21/02* (2006.01)
(Continued)

(52) U.S. Cl.
CPC ......... *G02B 23/243* (2013.01); *A61B 1/00188* (2013.01); *A61B 1/04* (2013.01);
(Continued)

(58) Field of Classification Search
CPC ..... G02B 21/02; G02B 13/04; G02B 27/0025; G02B 23/2484; G02B 5/005; G02B 23/2423; G02B 23/243; G02B 23/2407
(Continued)

(56) References Cited

U.S. PATENT DOCUMENTS 5,208,702 A * 5/1993 Shiraiwa .............. G02B 23/243
359/663
5,359,456 A 10/1994 Kikuchi
(Continued)

FOREIGN PATENT DOCUMENTS

JP 04315118 A 11/1992
JP 05107471 A 4/1993
(Continued)

OTHER PUBLICATIONS

International Search Report (ISR) dated Sep. 29, 2015 issued in International Application No. PCT/JP2015/072913.

*Primary Examiner* — Evelyn A Lester
(74) *Attorney, Agent, or Firm* — Holtz, Holtz & Volek PC

(57) ABSTRACT

An object of the present invention is to reduce the diameter, to make focus adjustment easy, and to achieve bright, wide-angle, high-resolution image quality.
Provided is an endoscope objective optical system including, in this order from the object side, a front group having negative refractive power, an aperture stop, and a positive rear group. The front group includes, in this order from the object side, a first lens, which is a single lens having negative refractive power, and a second lens, which is a single lens having positive refractive power. The rear group includes a third lens, which is a single lens having positive refractive power, a cemented lens formed of a fourth lens having positive refractive power and a fifth lens having negative refractive power, and a sixth lens having positive refractive power. The object-side surface of the first lens is a flat surface, the second lens has as meniscus shape, and the sixth lens is joined to the image-acquisition element, and the endoscope objective optical system satisfies the following conditional expression:

$$4 < Fno \times F6/F1\_5 < 500 \quad (1)$$

(Continued)

where Fno is the effective F number of the endoscope objective optical system, F6 is the focal length of the sixth lens, and F1_5 is the composite focal length of the first to fifth lenses.

10 Claims, 25 Drawing Sheets

(51) Int. Cl.
| | | |
|---|---|---|
| *A61B 1/06* | (2006.01) | |
| *G02B 23/24* | (2006.01) | |
| *G02B 9/62* | (2006.01) | |
| *G02B 27/00* | (2006.01) | |
| *A61B 1/00* | (2006.01) | |
| *A61B 1/04* | (2006.01) | |
| *G02B 5/00* | (2006.01) | |

(52) U.S. Cl.
CPC ............... *G02B 9/62* (2013.01); *G02B 13/04* (2013.01); *G02B 27/0025* (2013.01); *G02B 27/0081* (2013.01); *G02B 5/005* (2013.01); *G02B 21/02* (2013.01); *G02B 23/2407* (2013.01); *G02B 23/2423* (2013.01); *G02B 23/2484* (2013.01)

(58) Field of Classification Search
USPC ........ 359/656, 657, 658, 752, 761; 600/101, 600/160, 162, 167
See application file for complete search history.

(56) References Cited

U.S. PATENT DOCUMENTS

| | | | | |
|---|---|---|---|---|
| 5,587,839 | A * | 12/1996 | Miyano | G02B 23/243 359/660 |
| 5,916,148 | A * | 6/1999 | Tsuyuki | G02B 9/34 600/160 |
| 8,098,441 | B2 * | 1/2012 | Sasamoto | G02B 13/04 359/656 |
| 8,300,325 | B2 * | 10/2012 | Katahira | G02B 9/34 359/752 |
| 8,824,067 | B2 * | 9/2014 | Takato | G02B 23/2407 359/656 |
| 2004/0240081 | A1* | 12/2004 | Saito | G02B 23/243 359/754 |
| 2006/0007558 | A1* | 1/2006 | Hirata | G02B 21/33 359/656 |
| 2006/0061880 | A1* | 3/2006 | Kawakami | G02B 15/177 359/754 |
| 2008/0249367 | A1* | 10/2008 | Miyano | G02B 23/243 600/168 |
| 2009/0237807 | A1 | 9/2009 | Sasamoto | |
| 2010/0060993 | A1 | 3/2010 | Kanai et al. | |
| 2012/0127598 | A1 | 5/2012 | Katahira | |
| 2012/0147164 | A1 | 6/2012 | Sasamoto | |
| 2014/0198398 | A1* | 7/2014 | Kanazawa | A61B 1/00096 359/783 |
| 2014/0204475 | A1* | 7/2014 | Uzawa | G02B 23/243 359/738 |
| 2015/0177491 | A1 | 6/2015 | Cho et al. | |

FOREIGN PATENT DOCUMENTS

| | | |
|---|---|---|
| JP | 2006178242 A | 7/2006 |
| JP | 2010061007 A | 3/2010 |
| JP | 4695662 B2 | 6/2011 |
| JP | 4997348 B2 | 8/2012 |
| WO | 2011125539 A1 | 10/2011 |

* cited by examiner

ENDOSCOPE OBJECTIVE OPTICAL SYSTEM

CROSS-REFERENCE TO RELATED APPLICATIONS

This is a continuation of International Application PCT/JP2015/072913, with an international filing date of Aug. 13, 2015, which is hereby incorporated by reference herein in its entirety. This application claims the benefit of Japanese Patent Application No. 2014-174132, filed on Aug. 28, 2014, the content of which is incorporated herein by reference.

TECHNICAL FIELD

The present invention relates to an objective optical system, and, more specifically, it relates to an endoscope objective optical system applied to a medical endoscope.

BACKGROUND ART

In recent years, from the standpoint of reducing the burden on patients, improving diagnostic accuracy, etc., endoscopes have been reduced in size and improved in terms of image quality. Therefore, compact image-acquisition elements having high pixel numbers (for example, CODs and CMOSs) have been developed for use in endoscopes, and the pixel pitches thereof have been reduced year by year. As the pixel pitches are reduced, the endoscope objective optical systems are also required to be reduced in size, while achieving a wide angle of view and satisfying the required optical performance, such as aberration correction.

In general, when the pixel pitch of an image-acquisition element is reduced, the Fno needs to be reduced to make the objective optical system bright, otherwise a high-resolution image cannot be obtained. If the objective optical system is made bright, the depth of focus becomes small. Furthermore, in an objective optical system, after positioning, when the focus position is shifted due to, for example, displacement occurring when an adhesive is cured, the influence of a focus-position adjusting device, or the like.

Compact endoscope objective optical systems that can achieve high image quality are disclosed in, for example, 1 and 2. Specifically, PTL 1 discloses an endoscope objective optical system that has been reduced in diameter, has been made bright by reducing the Fno, has good various aberrations characteristics, and has been made less susceptible to one-side blur without increasing the power of the first lens. Furthermore, PTL 2 discloses an endoscope objective optical system that has good various aberrations characteristics.

CITATION LIST

Patent Literature

{Patent Literature 1} The Publication of Japanese Patent No. 4695662
{Patent Literature 2} The Publication of Japanese Patent No. 4997348

SUMMARY OF INVENTION

Technical Problem

Because the endoscope objective optical system in PTL 1 is a bright objective optical system having a reduced Fno, the depth of focus is small. Furthermore, because the sensitivity of the focus adjustment position is high, the influence of manufacturing variations on the image quality is large. Thus, stable production thereof is difficult.

The endoscope objective optical system in PTL 2 has low sensitivity of the focus adjustment position.

The problem associated with focus adjustment, which is caused by reducing the diameter, is not considered in either of the above-described endoscope objective optical systems. Hence, in order to optimize focus adjustment, for example, it is necessary to reduce the parts tolerance or to newly develop a high-precision focus adjustment device with which the focus position is not displaced after positioning.

The present invention is a small-diameter endoscope objective optical system with which focus adjustment is easy and with which bright, wide-angle, high-resolution image quality can be achieved.

Solution to Problem

An aspect of the present invention is an endoscope objective optical system including, in this order from an object side: a front group having negative refractive power as a whole; an aperture stop; and a rear group having positive refractive power as a whole. The front group includes, in this order from the object side, a first lens, which is a single lens having negative refractive power, and a second lens, which is a single lens having positive refractive power. The rear group includes, in this order from the object side, a third lens, which is a single lens having positive refractive power, a cemented lens formed of a fourth lens having positive refractive power and a fifth lens having negative refractive power, and a sixth lens having positive refractive power. An object-side surface of the first lens is a flat surface, the second lens has a meniscus shape, the sixth lens is joined to an image-acquisition element, and the endoscope objective optical system satisfies the following conditional expression:

$$4 < Fno \times F6/F1\_5 < 500 \tag{1}$$

where Fno is the effective F number of the endoscope objective optical system, F6 is the focal length of the sixth lens, and F1_5 is the composite focal length of the first to fifth lenses.

In the above-described aspect, it is preferable to satisfy the following conditional expression:

$$1.1 < SH\_R1R6 < 10 \tag{2}$$

where SH_R1R6=|(R1R+R6L)/(R1R−R6L)|, R1R is the radius of curvature of an image-side surface of the first lens, and R6L is the radius of curvature of an object-side surface of the sixth lens.

In the above-described aspect, it is preferable to satisfy the following conditional expression:

$$-1.5 < R4R/R6L < -0.01 \tag{3}$$

where R4R is the radius of curvature of an image-side surface of the fourth lens, and R6L is the radius of curvature of an object-side surface of the sixth lens.

In the above-described aspect, it is preferable to satisfy the following conditional expression:

$$2.2 < F23/FL < 4.0 \tag{4}$$

where F23 is the composite focal length of the second and third lenses, and FL is the composite focal length of the entire system.

In the above-described aspect, it is preferable to satisfy the following conditional expression:

$$-0.8 < F1/F6 < -0.01 \quad (5)$$

where F1 is the focal length of the first lens, and F6 is the focal length of the sixth lens.

In the above-described aspect, it is preferable to satisfy the following conditional expression:

$$0.0003 < P^2/(L \times F6) < 0.015 \quad (6)$$

where P is a distance between the fifth lens and the sixth lens, and L is the overall length of the endoscope objective optical system.

In the above-described aspect, it is preferable to satisfy the following conditional expression:

$$-2.0 < F12/F36 < -0.6 \quad (7)$$

where P12 is the composite focal length of the front group (first and second lenses), and F36 is the composite focal length of the rear group (from the third to sixth lenses).

In the above-described aspect, it is preferable to satisfy the following conditional expression:

$$0.05 < FL/L < 0.12 \quad (8)$$

In the above-described aspect, it is preferable to satisfy the following conditional expression:

$$0.06 < IH/L < 0.12 \quad (9)$$

where IH is the maximum image height.

In the above-described aspect, it is preferable to satisfy the following conditional expression:

$$\omega > 62° \quad (10)$$

where $\omega$ is the half angle of view.

DESCRIPTION OF EMBODIMENTS

Endoscope objective optical systems according to examples of the present invention will be described below with reference to the drawings.

Figure 1:
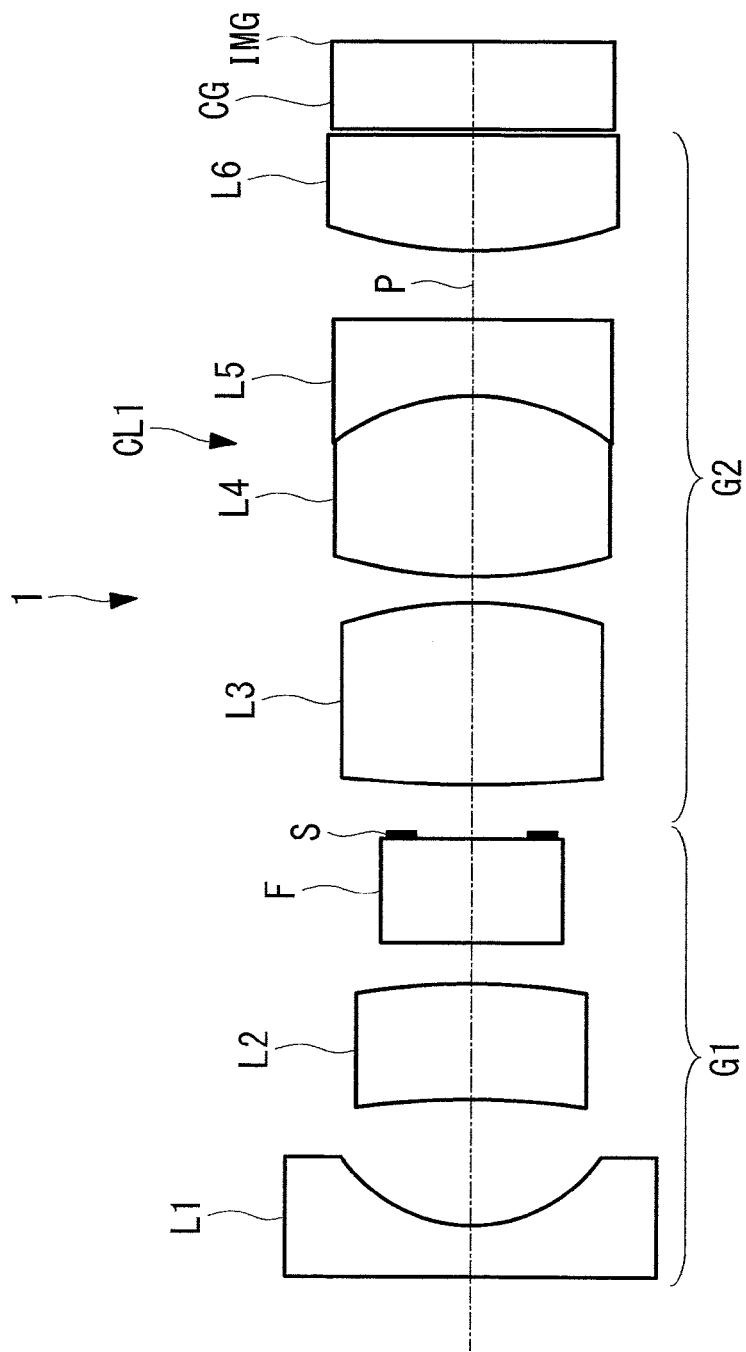
FIG. 1 is a cross-sectional view showing the overall configuration of an endoscope objective optical system according to an embodiment of the present invention.

As shown in FIG. 1, an endoscope objective optical system includes, in this order from the object side, a front group G1 having negative refractive power as a whole, an aperture stop S, and a rear group G2 having positive refractive power as a whole.

The front group G1 includes, in this order from the object side, a first lens L1, which is a single lens having a flat surface on the object side and has negative refractive power; a second lens L2, which is a single lens having a meniscus shape and has positive refractive power; and a parallel plate F, which serves as an infrared cut filter.

The rear group G2 includes a third lens, which is a single lens having positive refractive power; a cemented lens CL1 formed by joining together a fourth lens L4 having positive refractive power and a fifth lens L5 having negative refractive power; and a sixth lens L6, which is joined to a cover glass CG of an image-acquisition element and has positive refractive power.

In FIG. 1, reference sign "P" shown within the rear group G2 denotes a focus adjustment position (a distance between the fifth lens L5 and the sixth lens L6).

The endoscope objective optical system is configured to satisfy Conditional Expressions (1) to (10) below.

$$4 < Fno \times F6/F1\_5 < 500 \qquad (1)$$

where Fno is the effective F number of the endoscope objective optical system, F6 is the focal length of the sixth lens, and F1_5 is the composite focal length of the first to fifth lenses.

Conditional Expression (1) relates to the sensitivity of the focus adjustment position. In Conditional Expression (1), if Fno×F6/F1_5 is larger than the upper limit, when it is intended to achieve bright, high-resolution image quality, the radius of curvature of the sixth lens is large, and, as a result, the sensitivity of the focus adjustment position is large. Thus, the endoscope objective optical system is susceptible to focus shift. On the other hand, in Conditional Expression (1), if the lower limit is exceeded, the radius of curvature of the sixth lens is too small, making the field curvature large. Hence, it is difficult to obtain good image quality. Furthermore, processing of the sixth lens is difficult.

It is preferable to satisfy Conditional Expression (1'), instead of Conditional Expression (1), and it is more preferable to satisfy Conditional Expression (1"), instead of Conditional Expression (1) or (1').

$$6 < Fno \times F6/F1\_5 < 120 \qquad (1')$$

$$7 < Fno \times F6/F1\_5 < 25 \qquad (1'')$$

$$1.1 < SH\_R1R6 < 10 \qquad (2)$$

where $SH\_R1R6 = |(R1R+R6L)/(R1R-R6L)|$, R1R is the radius of curvature of the image-side surface of the first lens, and R6L is the radius of curvature of the object-side surface of the sixth lens.

Conditional Expression (2) relates to field curvature. By satisfying Conditional Expression (2), the power balance between the first lens and the sixth lens can be appropriately maintained, and hence, it is possible to appropriately correct field curvature and to improve the image quality of the image to be acquired. In Conditional Expression (2), if SH_R1R6 is larger than the upper limit, the power balance between the first lens and the sixth lens is disrupted, making it impossible to appropriately correct field curvature. Thus, it is difficult to obtain good image quality. Furthermore, processing of the sixth lens is difficult. On the other hand, if the lower limit is exceeded, although various aberrations can be appropriately corrected, the optical system is susceptible to focus shift.

It is preferable to satisfy Conditional Expression (2'), instead of Conditional Expression (2), and it is more preferable to satisfy Conditional Expression (2"), instead of Conditional Expression (2) or (2').

$$1.2 < SH\_R1R6 < 7 \qquad (2')$$

$$2.0 < SH\_R1R6 < 5 \qquad (2'')$$

$$-1.5 < R4R/R6L < -0.01 \qquad (3)$$

where R4R is the radius of curvature of the image-side surface of the fourth lens, and R6L is the radius of curvature of the object-side surface of the sixth lens.

Conditional Expression (3) relates to the ease of processing of lenses. By satisfying Conditional Expression (3), processing of lenses can be made easy, and the image quality of the image to be acquired can be improved. If the upper limit of Conditional Expression (3) is exceeded, the edge thickness of the fourth lens is too small, making processing difficult. On the other hand, if the lower limit is exceeded, the edge thickness of the sixth lens is too small, making processing difficult. Furthermore, because field curvature increases, it is difficult to achieve high-resolution image quality.

It is preferable to satisfy Conditional Expression (3'), instead of Conditional Expression (3), and it is more preferable to satisfy Conditional Expression (3"), instead of Conditional Expression (3) or (3').

$$-1.2 < R4R/R6L < -0.05 \qquad (3')$$

$$-1.0 < R4R/R6L < -0.15 \qquad (3'')$$

$$2.2 < F23/FL < 4.0 \qquad (4)$$

where F23 is the composite focal length of the second and third lenses, and FL is the composite focal length of the entire system.

By satisfying Conditional Expression (4), it is possible to suppress manufacturing variations. If the lower limit of Conditional Expression (4) is exceeded, because the positive power is strong, the negative power of the first lens is strong, making one-side blur easy to occur and making the optical system susceptible to manufacturing variations. If the upper limit of Conditional Expression (4) is exceeded, it is difficult to achieve a compact size.

It is preferable to satisfy Conditional Expression (4'), instead of Conditional Expression (4), and it is more preferable to satisfy Conditional Expression (4"), instead of Conditional Expression (4) or (4').

$$2.2 < F23/FL < 3.7 \tag{4'}$$

$$2.3 < F23/FL < 3.4 \tag{4''}$$

$$-0.8 < F1/F6 < -0.01 \tag{5}$$

where F1 is the focal length of the first lens, and F6 is the focal length of the sixth lens.

By satisfying Conditional Expression (5), it is possible to make the optical system less susceptible to manufacturing variations and to contribute to achieving a compact size. If the upper limit of Conditional Expression (5) is exceeded, it is difficult to achieve a compact size, and the various aberrations characteristics are deteriorated, making it difficult to obtain good image quality. On the other hand, in Conditional Expression (5), if the lower limit is exceeded, the endoscope objective optical system is susceptible to one-side blur, focus shift, and manufacturing variations.

It is preferable to satisfy Conditional Expression (5'), instead of Conditional Expression (5), and it is more preferable to satisfy Conditional Expression (5"), instead of Conditional Expression (5) or (5').

$$-0.6 < F1/F6 < -0.02 \tag{5'}$$

$$-0.4 < F1/F6 < -0.1 \tag{5''}$$

$$0.0003 < P^2/(L \times F6) < 0.015 \tag{6}$$

where P is a distance between the fifth lens and the sixth lens, and L is the overall length of the endoscope objective optical system.

By satisfying Conditional Expression (6), focus adjustment can be made easy. In Conditional Expression (6), if the value of $P^2/L$ is small, a sufficient focus adjustment distance cannot be obtained, so, the focus sensitivity needs to be increased. Therefore, the value of F6 needs to be increased. In Conditional Expression (6), if the lower limit is exceeded, the optical system is susceptible to focus shift. On the other hand, in Conditional Expression (6), if the upper limit is exceeded, correction of various aberrations is difficult.

It is preferable to satisfy Conditional Expression (6'), instead of Conditional Expression (6), and it is more preferable to satisfy Conditional Expression (6"), instead of Conditional Expression (6) or (6').

$$0.0005 < P^2/(L \times F6) < 0.013 \tag{6'}$$

$$0.001 < P^2/(L \times F6) < 0.01 \tag{6''}$$

$$-2.0 < F12/F36 < -0.6 \tag{7}$$

where F12 is the composite focal length of the front group (the first and second lenses), and F36 is the composite focal length of the rear group (from the third to sixth lenses).

By satisfying Conditional Expression (7), the appropriate focal length of the rear group can be maintained. In Conditional Expression (7), if the upper limit is exceeded, the focal length of the rear group is relatively large, and the image plane tilts toward the minus side. Hence, it is difficult to suppress various aberrations and to achieve good image quality. On the other hand, in Conditional Expression (7), if the lower limit is exceeded, the focal length of the rear group is relatively small, R of the lenses in the rear group is small, and the edge thicknesses of the lenses is too small. Hence, processing of the rear group lenses is difficult.

It is preferable to satisfy Conditional Expression (7'), instead of Conditional Expression (7), and it is more preferable to satisfy Conditional Expression (7"), instead of Conditional Expression (7) or (7').

$$-1.7 < F12/F36 < -0.6 \tag{7'}$$

$$-1.4 < F12/F36 < -0.6 \tag{7''}$$

$$0.05 < FL/L < 0.12 \tag{8}$$

By satisfying Conditional Expression (8), it is possible to achieve a compact size and a wide angle of view. In Conditional Expression (8), if the upper limit is exceeded, it is difficult to achieve a wide angle of view, whereas if the lower limit is exceeded, it is difficult to achieve a compact size.

It is preferable to satisfy Conditional Expression (8'), instead of Conditional Expression (8), and it is more preferable to satisfy Conditional Expression (8"), instead of Conditional Expression (8) or (8').

$$0.06 < FL/L < 0.12 \tag{8'}$$

$$0.07 < FL/L < 0.12 \tag{8''}$$

$$0.06 < IH/L < 0.12 \tag{9}$$

where IH is the maximum image height.

By satisfying Conditional Expression (9), it is possible to achieve a compact size and to improve the ease of production. In Conditional Expression (9), if the lower limit is exceeded, it is difficult to achieve a compact size, whereas if the upper limit is exceeded, the optical system is susceptible to manufacturing variations, making stable production difficult.

It is preferable to satisfy Conditional Expression (9'), instead of Conditional Expression (9), and it is more preferable to satisfy Conditional Expression (9"), instead of Conditional Expression (9) or (9').

$$0.07 < IH/L < 0.12 \tag{9'}$$

$$0.07 < IH/L < 0.11 \tag{9''}$$

$$\omega > 62° \tag{10}$$

where ω is the half angle of view.

By satisfying Conditional Expression (10), it is possible to reduce the risk of failing to find a lesion during in vivo screening. Specifically, by satisfying Conditional Expression (10), it is possible to ensure a half angle of view of 62° and to maintain a wide angle.

It is preferable to satisfy Conditional Expression (10'), instead of Conditional Expression (10).

$$\omega > 65° \tag{10'}$$

As has been described above, in this embodiment, the lenses constituting the front group G1 include: the first lens L1, which is a piano-concave lens having a flat surface on the object plane side and has negative refractive power, the first lens L1 being disposed on the extreme object side; and the second lens L2, which is a single lens having a meniscus shape and has positive refractive power, the second lens L2 being disposed on the image side of the first lens. With this configuration, water drainage during observation is improved and breakage due to an impact is reduced while establishing a retro-focus configuration with the first lens L1. Furthermore, the second lens corrects aberrations of the first lens L1 and converges light without increasing the lens diameter. Hence, it is possible to achieve a compact, high-performance objective optical system that has a reduced number of lenses, is suitable for an endoscope, and enables bright, wide-angle, high-resolution image quality to be acquired.

In addition, by making the rear group G2 have positive refractive power so as to contribute mainly to image formation, and by providing the third lens L3 and the fourth lens L4, which both have positive refractive power, as the lenses constituting the rear group, generation of aberrations is suppressed, and the power needed to achieve a compact size is distributed even though the Fno is small and the brightness is ensured.

Furthermore, in the rear group G2, by making the fourth lens L4 disposed on the image side a cemented lens CL1 joined to the negative fifth lens L5, a positive-and-negative cemented lens is disposed at a position where the peripheral ray height is high. Thus, it is possible to correct chromatic aberration.

Furthermore, by providing the sixth lens L6, which is joined to the image-acquisition element (cover glass CG) and has positive refractive power, on the image side of the rear group G2, it is possible to reduce the optical magnification of the first lens L1 to the fifth lens L5 and to weaken the sensitivity of the focus adjustment position.

By doing so, focus adjustment is made easy, that is, ease of assembly is improved, making it possible to suppress manufacturing variations.

EXAMPLES

Now, Examples 1 to 8 of the wide-angle objective optical system according to the above-described embodiment will be described with reference to FIGS. 2 to 17. In the lens data presented in the respective examples, r indicates the radius of curvature (unit: mm), d indicates the inter-surface distance (mm), Ne indicates the refractive index with respect to the e-line, and vd indicates the Abbe number.

Example 1

Figure 2:
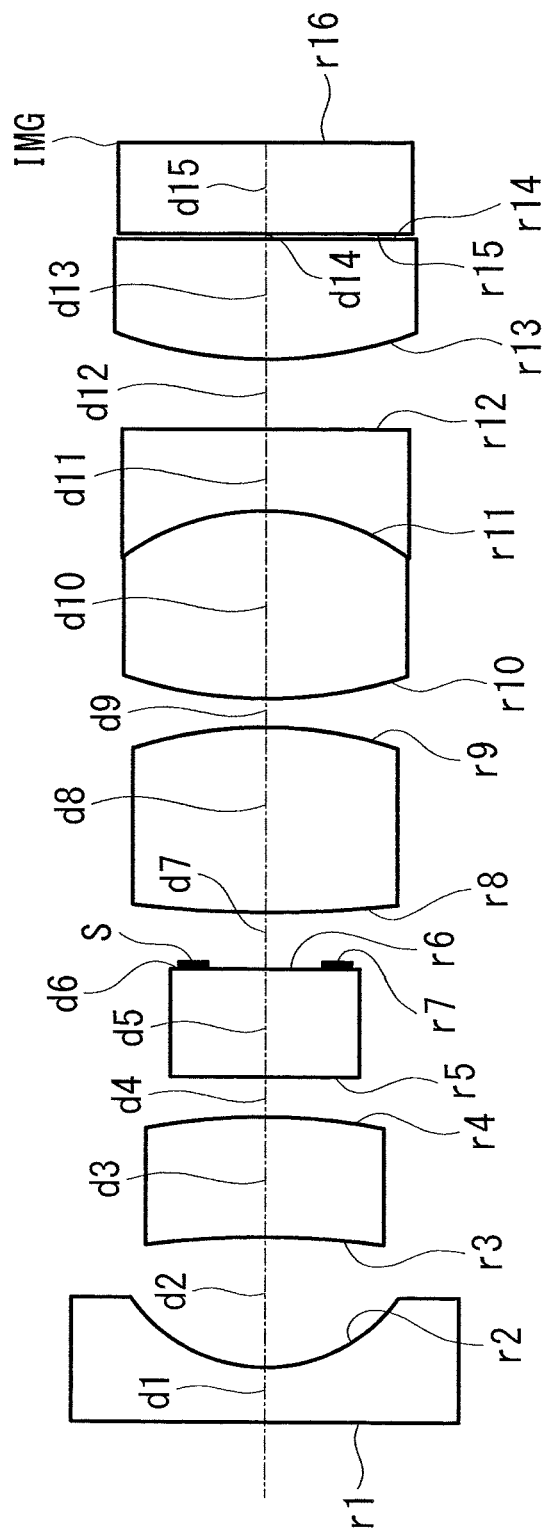
FIG. 2 is a cross-sectional view showing the overall configuration of an endoscope objective optical system according to Example 1 of the present invention.
Figure 3A:
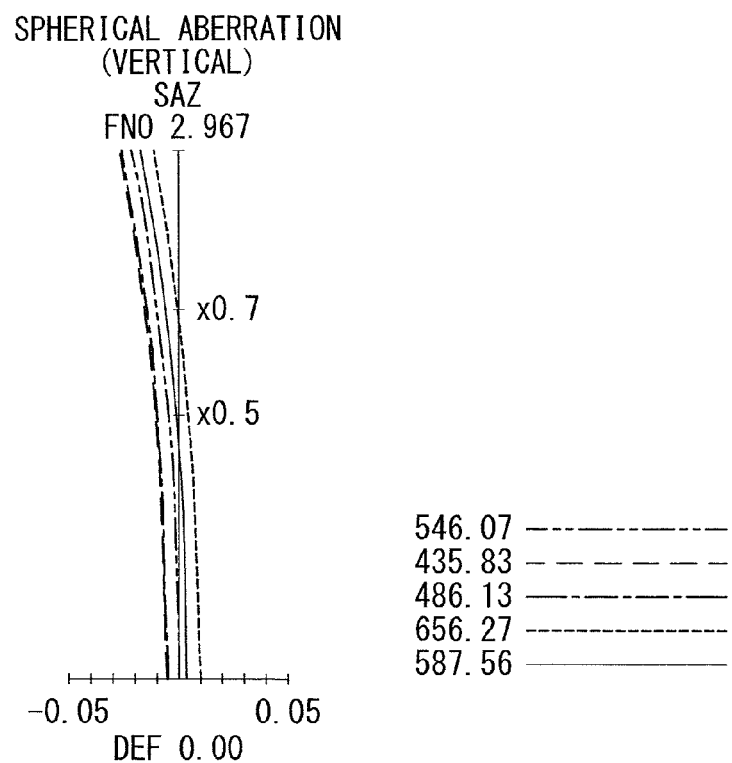
FIG. 3A is an aberration diagram of the endoscope objective optical system according to Example 1 of the present invention.
Figure 3B:
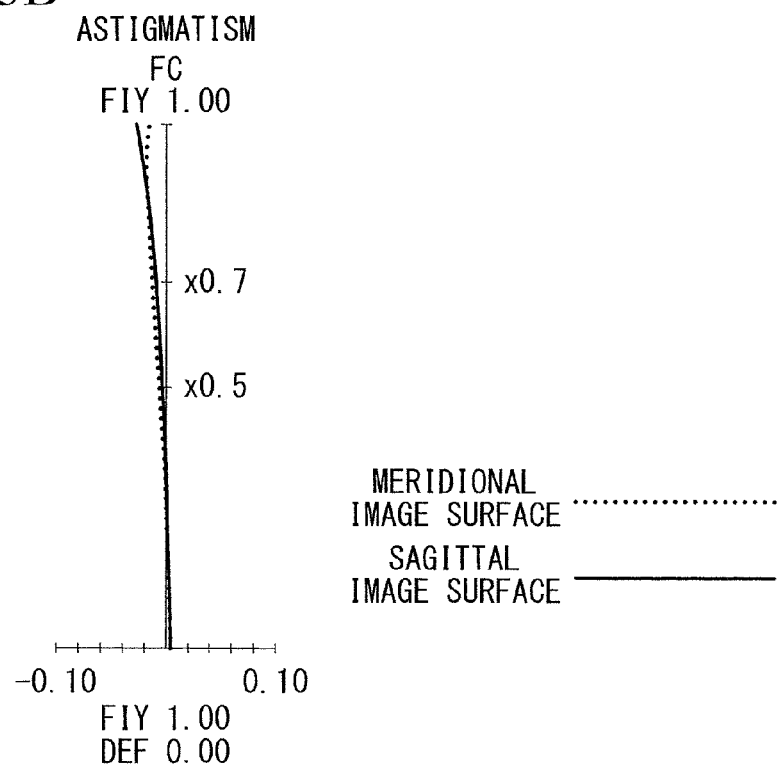
FIG. 3B is an aberration diagram of the endoscope objective optical system according to Example 1 of the present invention.
Figure 3C:
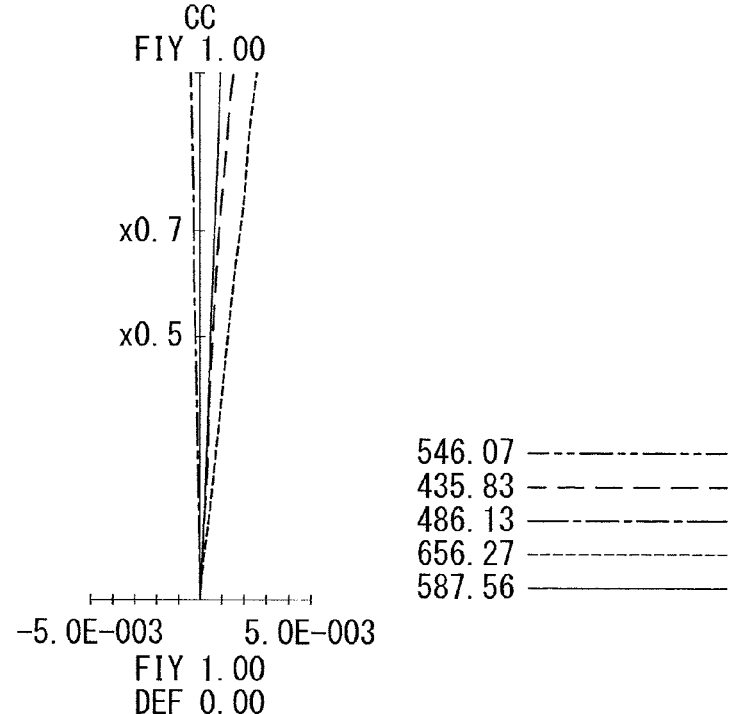
FIG. 3C is an aberration diagram of the endoscope objective optical system according to Example 1 of the present invention.
Figure 3D:
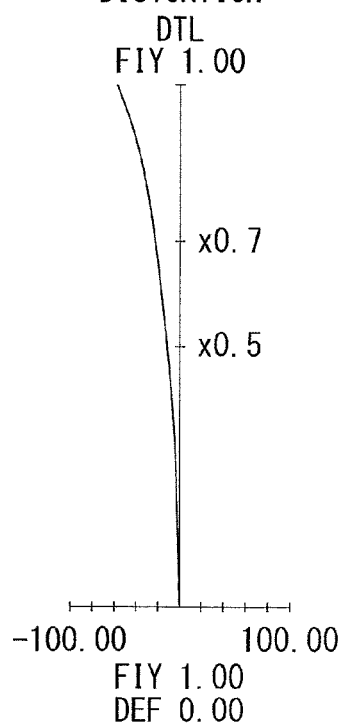
FIG. 3D is an aberration diagram of the endoscope objective optical system according to Example 1 of the present invention.

The overall configuration of the endoscope objective optical system according to Example 1 of the present invention is shown in FIG. 2, and the lens data thereof is shown below. Furthermore, aberration diagrams of the endoscope objective optical system according to this example are shown in FIGS. 3A to 3D.

Lens Data

| Surface Number | r | d | Ne | vd |
|---|---|---|---|---|
| object plane | ∞ | 26.7261 | | |
| 1 | ∞ | 0.4454 | 1.88815 | 40.76 |
| 2 | 1.3675 | 1.0690 | | |
| 3 | −10.2962 | 1.0022 | 1.93429 | 18.90 |
| 4 | −5.6258 | 0.3341 | | |
| 5 | ∞ | 0.8909 | 1.49557 | 75.00 |
| 6 (stop) | ∞ | 0.0668 | | |
| 7 | ∞ | 0.4009 | | |
| 8 | 9.4766 | 1.5590 | 1.88815 | 40.76 |
| 9 | −3.5835 | 0.2227 | | |
| 10 | 3.9243 | 1.5590 | 1.69979 | 55.53 |
| 11 | −1.9065 | 0.6682 | 1.93429 | 18.90 |
| 12 | ∞ | 0.5791 | | |
| 13 | 3.5835 | 1.0022 | 1.51825 | 64.14 |
| 14 | ∞ | 0.0223 | 1.51500 | 64.00 |
| 15 | ∞ | 0.7795 | 1.50700 | 63.26 |
| 16 | image-acquisition surface | | | |

Miscellaneous Data

| | |
|---|---|
| Focal Length | 1.047 |
| Fno | 2.979 |
| Half Angle of View | 66.7° |
| Image Height | 1.000 |
| Overall Length | 10.60 |

Example 2

Figure 4:
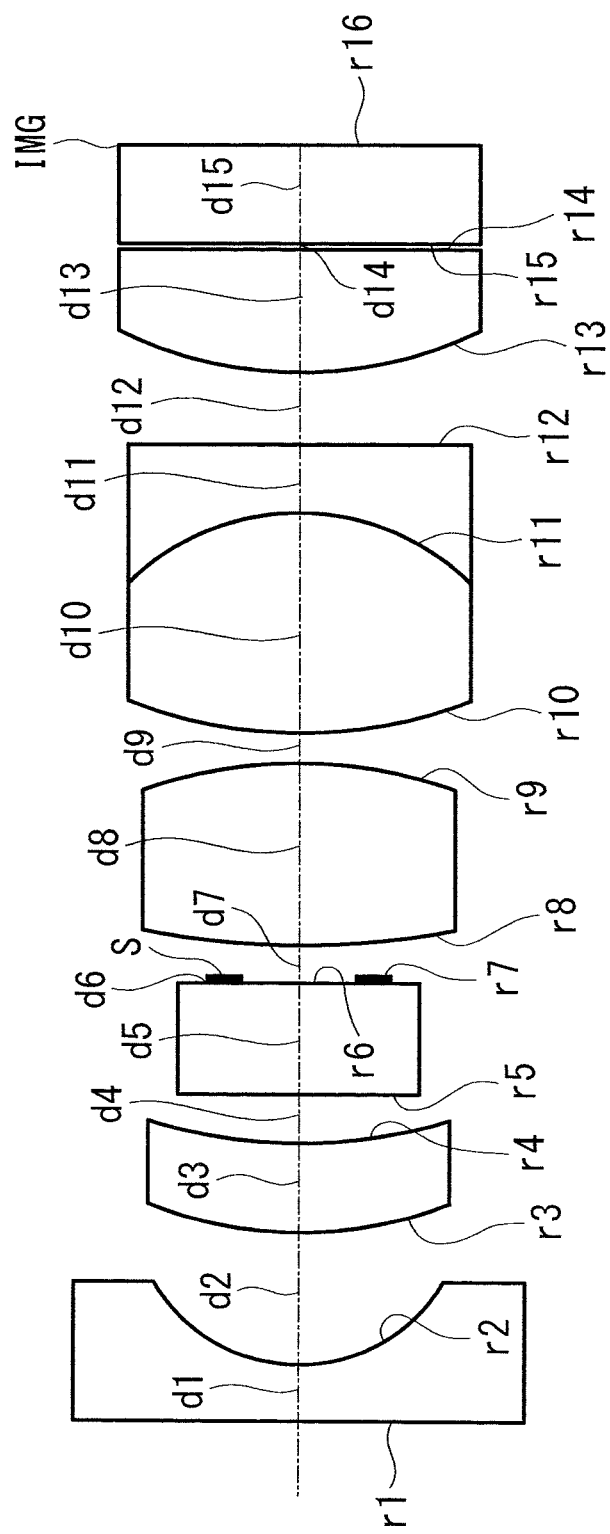
FIG. 4 is a cross-sectional view showing the overall configuration of an endoscope objective optical system according to Example 2 of the present invention.
Figure 5A:
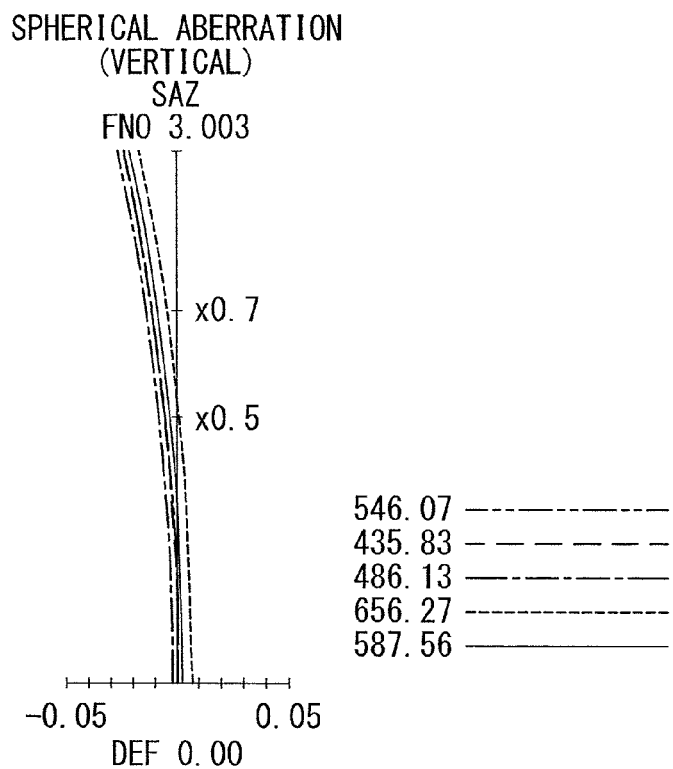
FIG. 5A is an aberration diagram of the endoscope objective optical system according to Example 2 of the present invention.
Figure 5B:
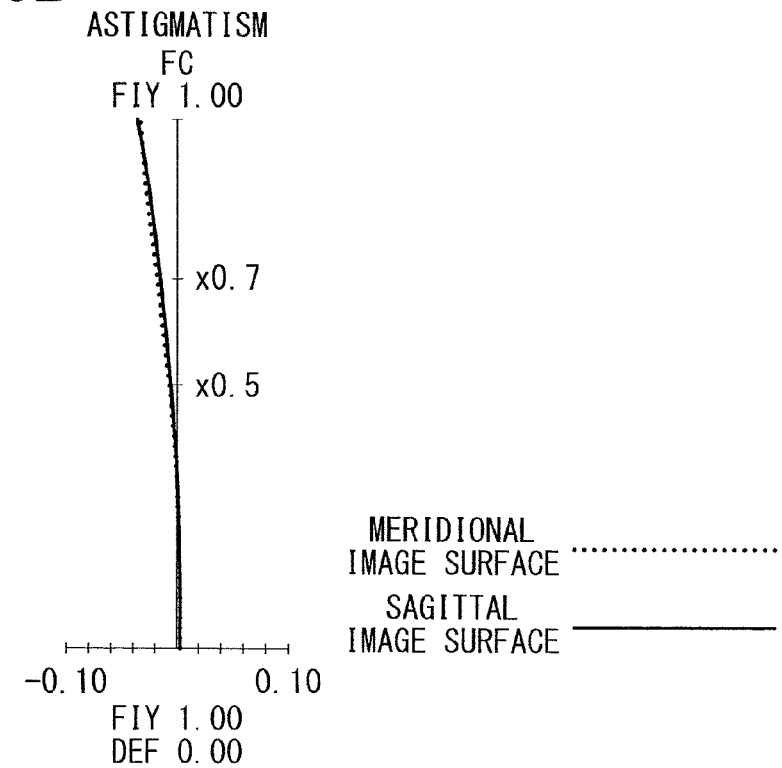
FIG. 5B is an aberration diagram of the endoscope objective optical system according to Example 2 of the present invention.
Figure 5C:
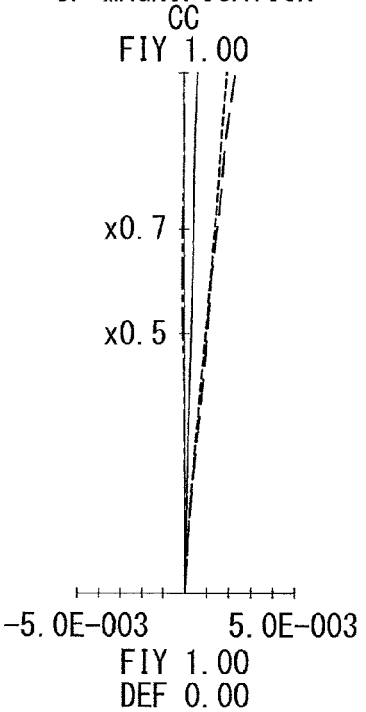
FIG. 5C is an aberration diagram of the endoscope objective optical system according to Example 2 of the present invention.
Figure 5D:
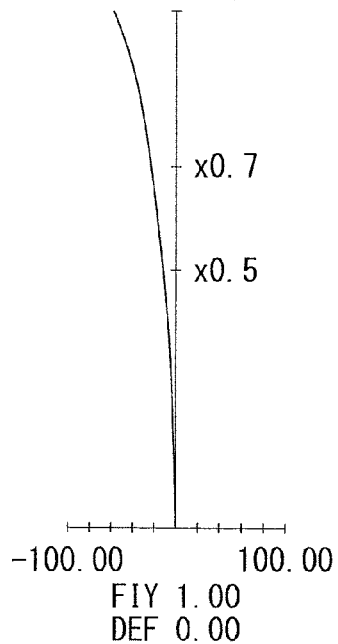
FIG. 5D is an aberration diagram of the endoscope objective optical system according to Example 2 of the present invention.

The overall configuration of the endoscope objective optical system according to Example 2 of the present invention is shown, in FIG. 4, and the lens data thereof is shown below. Furthermore, aberration diagrams of the endoscope objective optical system according to this example are shown in FIGS. 5A to 5D.

Lens Data

| Surface Number | r | d | Ne | vd |
|---|---|---|---|---|
| object plane | ∞ | 24.9443 | | |
| 1 | ∞ | 0.4887 | 1.88815 | 40.76 |
| 2 | 1.2969 | 1.0452 | | |
| 3 | 3.2461 | 0.7126 | 1.93429 | 18.90 |
| 4 | 3.9951 | 0.3873 | | |
| 5 | ∞ | 0.8909 | 1.51500 | 75.00 |
| 6 (stop) | ∞ | 0.0668 | | |
| 7 | ∞ | 0.2221 | | |
| 8 | 6.3541 | 1.4474 | 1.83945 | 42.71 |
| 9 | −3.5783 | 0.2223 | | |
| 10 | 3.2639 | 1.7463 | 1.69979 | 55.53 |
| 11 | −1.8928 | 0.5568 | 1.93429 | 18.90 |
| 12 | ∞ | 0.5738 | | |
| 13 | 3.1989 | 1.0022 | 1.51825 | 64.14 |
| 14 | ∞ | 0.0223 | 1.51500 | 64.00 |
| 15 | ∞ | 0.7795 | 1.50700 | 63.26 |
| 16 | image-acquisition Surface | | | |

Miscellaneous Data

| | |
|---|---|
| Focal Length | 1.092 |
| Fno | 3.019 |
| Half Angle of View | 65.4° |

| Miscellaneous Data | |
|---|---|
| Image Height | 1.000 |
| Overall Length | 10.12 |

Example 3

Figure 6:
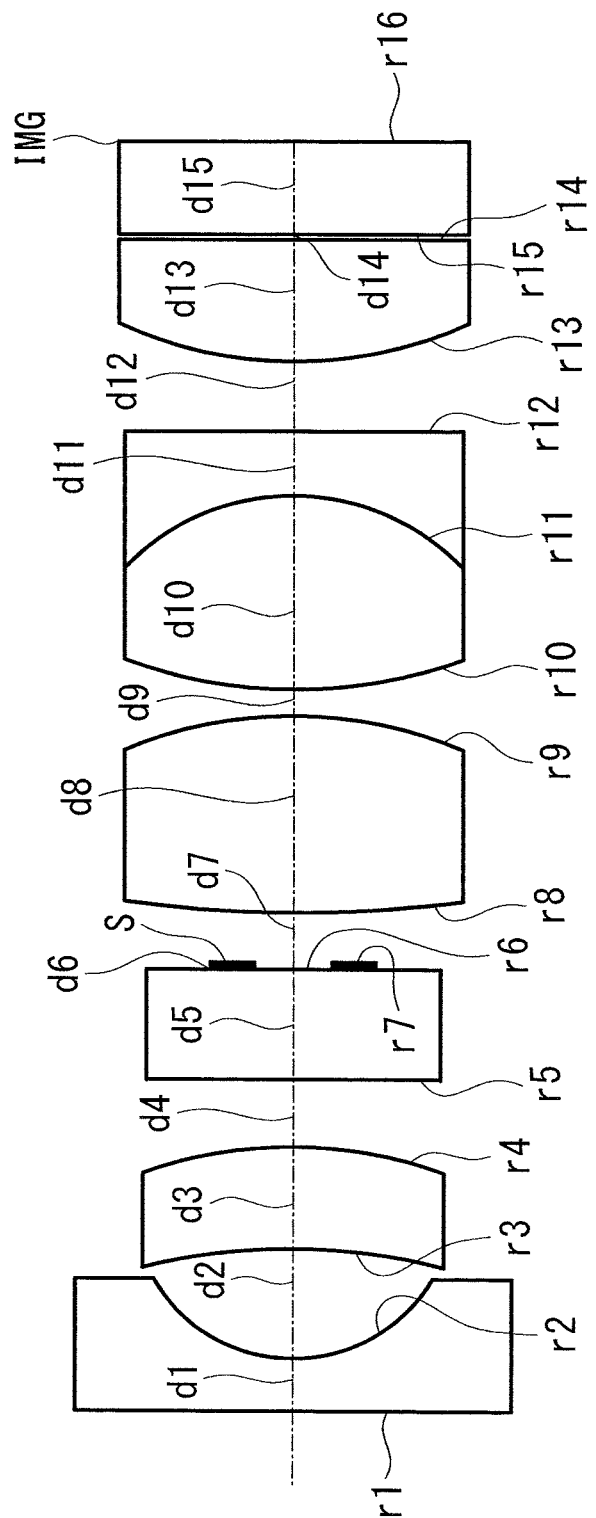
FIG. 6 is a cross-sectional view showing the overall configuration of an endoscope objective optical system according to Example 3 of the present invention.
Figure 7A:
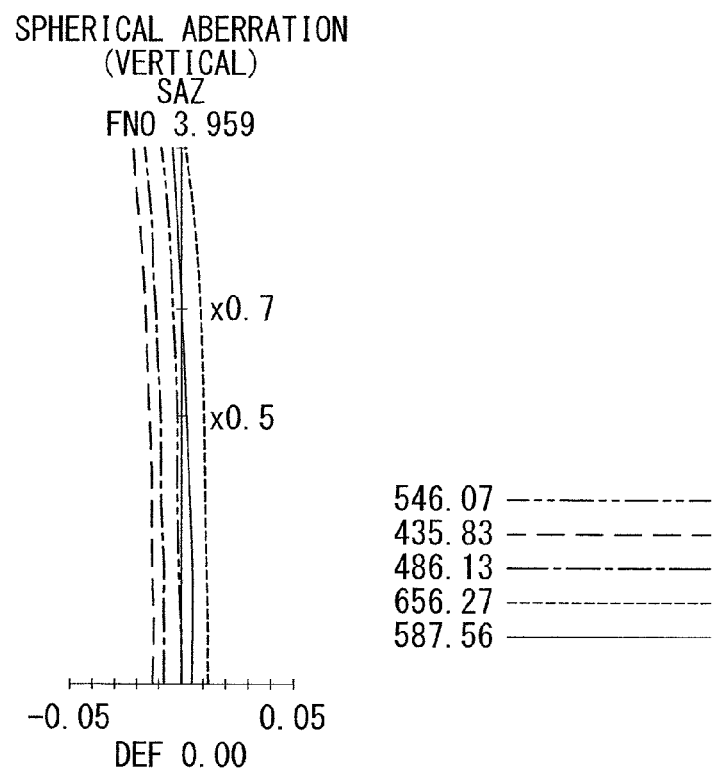
FIG. 7A is an aberration diagram of the endoscope objective optical system according to Example 3 of the present invention.
Figure 7B:
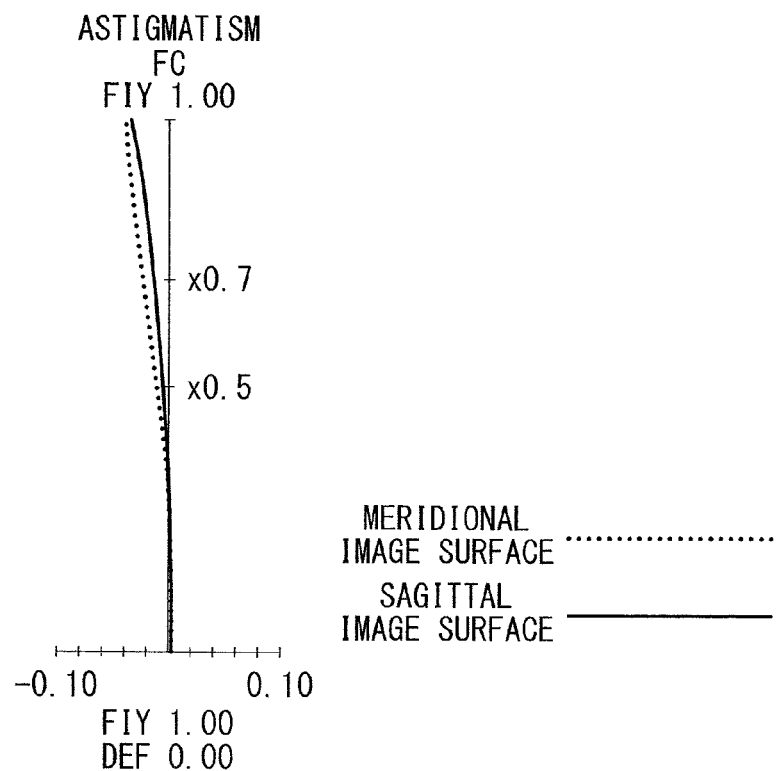
FIG. 7B is an aberration diagram of the endoscope objective optical system according to Example 3 of the present invention.
Figure 7C:
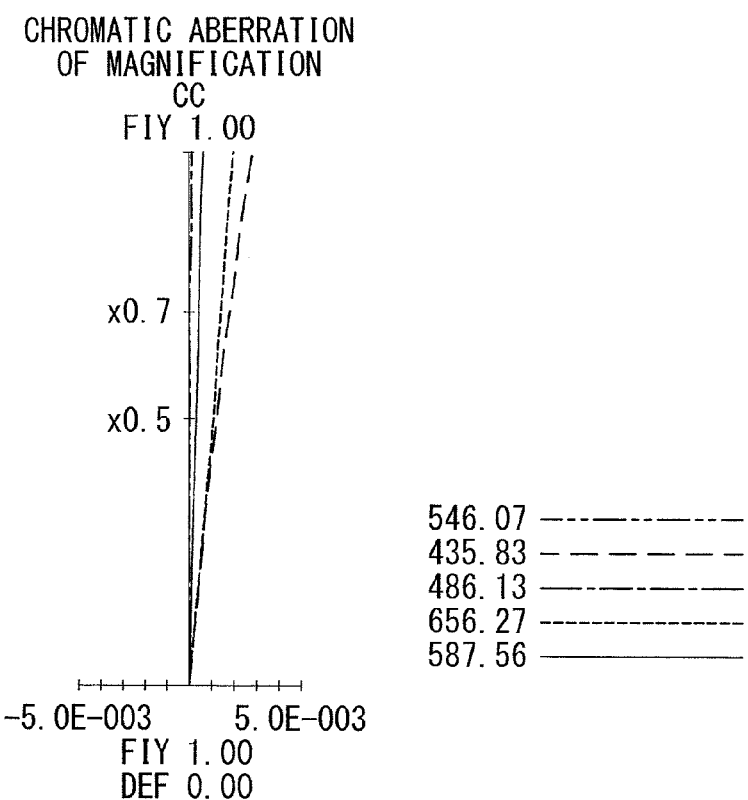
FIG. 7C is an aberration diagram of the endoscope objective optical system according to Example 3 of the present invention.
Figure 7D:
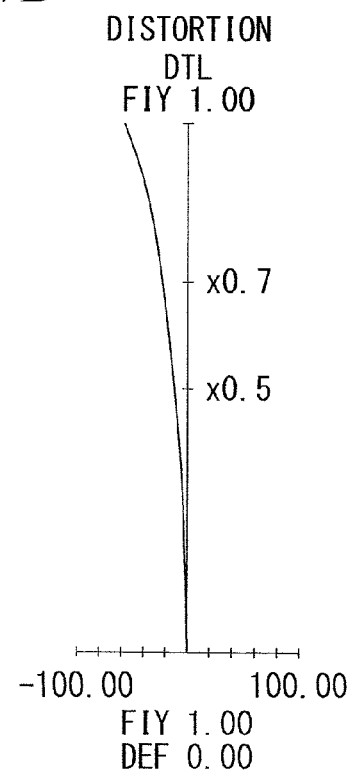
FIG. 7D is an aberration diagram of the endoscope objective optical system according to Example 3 of the present invention.

The overall configuration of the endoscope objective optical system according to Example 3 of the present invention is shown in FIG. 6, and the lens data thereof is shown below. Furthermore, aberration diagrams of the endoscope objective optical system according to this example are shown in FIGS. 7A to 7D.

| Lens Data | | | | |
|---|---|---|---|---|
| Surface Number | r | d | Ne | vd |
| object plane | ∞ | 26.7261 | | |
| 1 | ∞ | 0.4476 | 1.88815 | 40.76 |
| 2 | 1.3211 | 0.8682 | | |
| 3 | −4.7713 | 0.8238 | 1.93429 | 18.90 |
| 4 | −3.3911 | 0.5791 | | |
| 5 | ∞ | 0.8909 | | |
| 6 (stop) | ∞ | 0.0668 | | |
| 7 | ∞ | 0.3720 | | |
| 8 | 9.3689 | 1.6091 | 1.88815 | 40.76 |
| 9 | −3.5637 | 0.2222 | | |
| 10 | 4.0031 | 1.5583 | 1.69979 | 55.53 |
| 11 | −1.8967 | 0.5587 | 1.93429 | 18.90 |
| 12 | ∞ | 0.5663 | | |
| 13 | 3.3105 | 1.0022 | 1.51825 | 64.14 |
| 14 | ∞ | 0.0223 | 1.51500 | 64.00 |
| 15 | ∞ | 0.7795 | 1.50700 | 63.26 |
| 16 | image-acquisition Surface | | | |

| Miscellaneous Data | |
|---|---|
| Focal Length | 1.038 |
| Fno | 3.975 |
| Half Angle of View | 66.5° |
| Image Height | 1.000 |
| Overall Length | 10.37 |

Example 4

Figure 8:
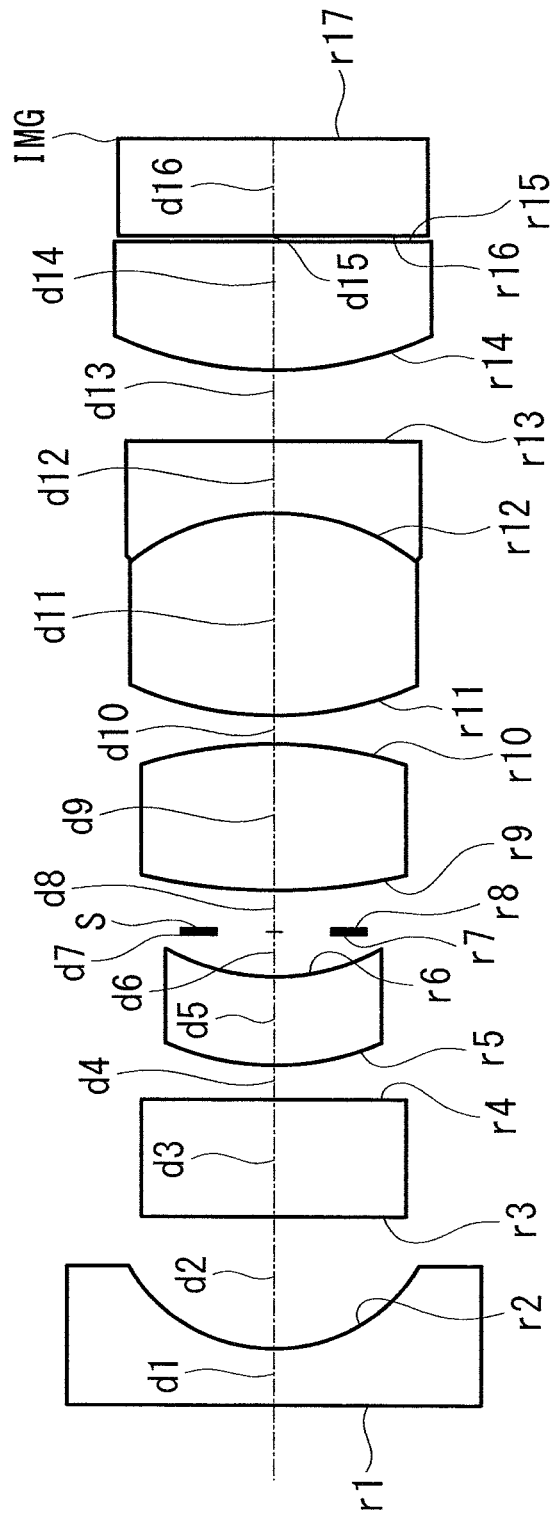
FIG. 8 is a cross-sectional view showing the overall configuration of an endoscope objective optical system according to Example 4 of the present invention.
Figure 9A:
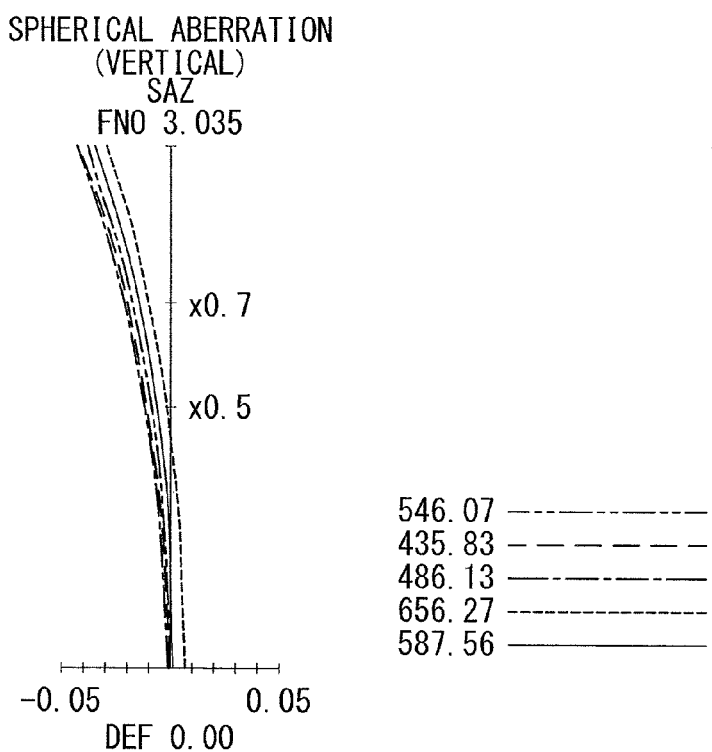
FIG. 9A is an aberration diagram of the endoscope objective optical system according to Example 4 of the present invention.
Figure 9B:
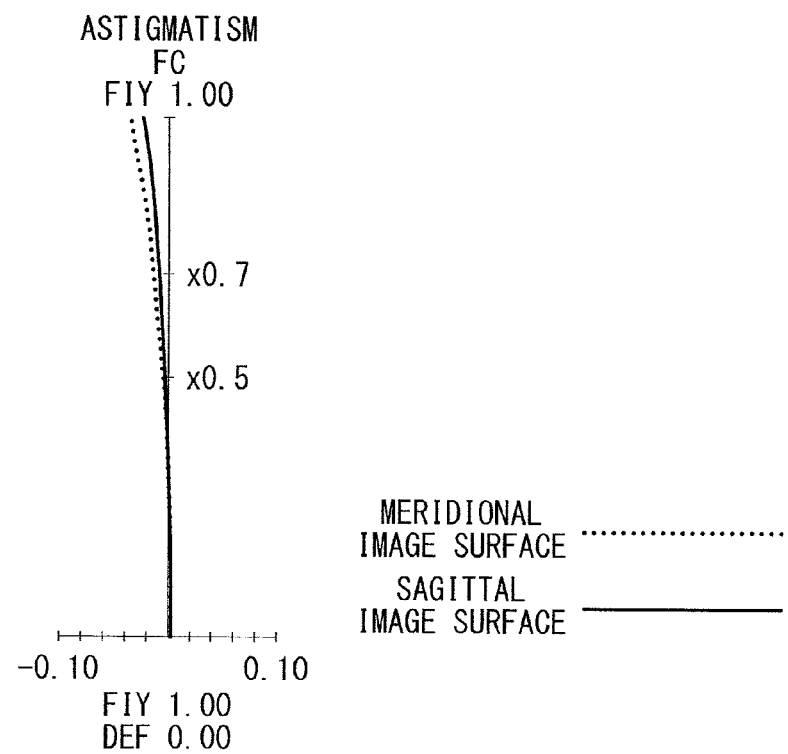
FIG. 9B is an aberration diagram of the endoscope objective optical system according to Example 4 of the present invention.
Figure 9C:
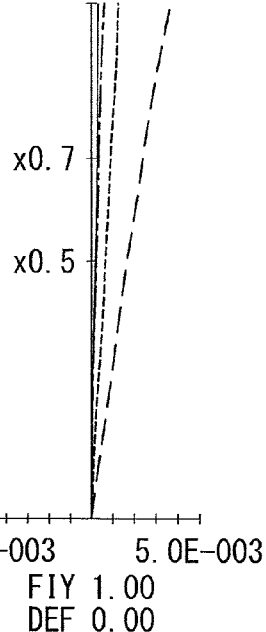
FIG. 9C is an aberration diagram of the endoscope objective optical system according to Example 4 of the present invention.
Figure 9D:
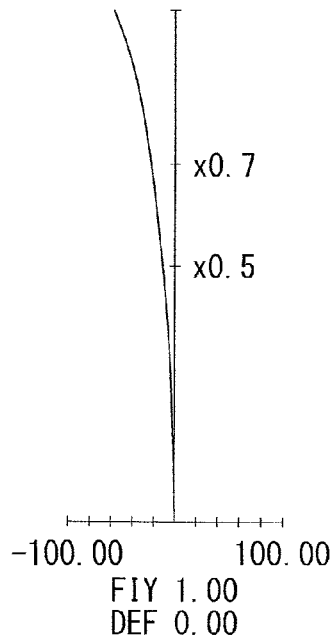
FIG. 9D is an aberration diagram of the endoscope objective optical system according to Example 4 of the present invention.

The overall configuration of the endoscope objective optical system according to Example 4 of the present invention is shown in FIG. 8, and the lens data thereof is shown below. Furthermore, aberration diagrams of the endoscope objective optical system according to this example are shown in FIGS. 9A to 9D.

| Lens Data | | | | |
|---|---|---|---|---|
| Surface Number | r | d | Ne | vd |
| object plane | ∞ | 26.0579 | | |
| 1 | ∞ | 0.4485 | 1.88815 | 440.76 |
| 2 | 1.2941 | 1.0110 | | |
| 3 | ∞ | 0.8909 | 1.51500 | 75.00 |
| 4 | ∞ | 0.2636 | | |
| 5 | 1.9246 | 0.6927 | 1.93429 | 18.90 |
| 6 | 1.7733 | 0.3211 | | |
| 7 (stop) | ∞ | 0.0668 | | |
| 8 | ∞ | 0.2930 | | |
| 9 | 4.9425 | 1.1191 | 1.82017 | 46.62 |
| 10 | −3.2375 | 0.2221 | | |
| 11 | 2.8952 | 1.5588 | 1.64129 | 55.38 |
| 12 | −1.7817 | 0.5566 | 1.93429 | 18.90 |
| 13 | 171.5852 | 0.5563 | | |
| 14 | 3.1170 | 1.0022 | 1.51825 | 64.14 |
| 15 | ∞ | 0.0223 | 1.51500 | 64.00 |
| 16 | ∞ | 0.7795 | 1.50700 | 63.26 |
| 17 | image-acquisition Surface | | | |

| Miscellaneous Data | |
|---|---|
| Focal Length | 1.091 |
| Fno | 3.054 |
| Half Angle of View | 66.0° |
| Image Height | 1.000 |
| Overall Length | 9.80 |

Example 5

Figure 10:
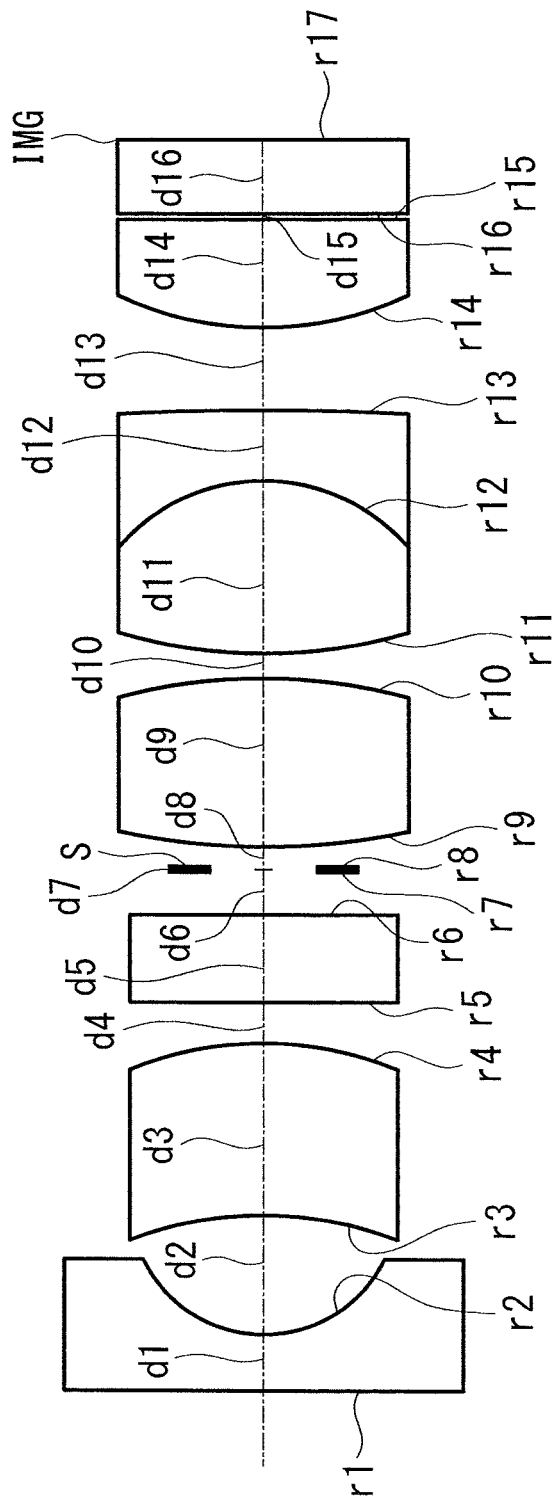
FIG. 10 is a cross-sectional view showing the overall configuration of an endoscope objective optical system according to Example 5 of the present invention.
Figure 11A:
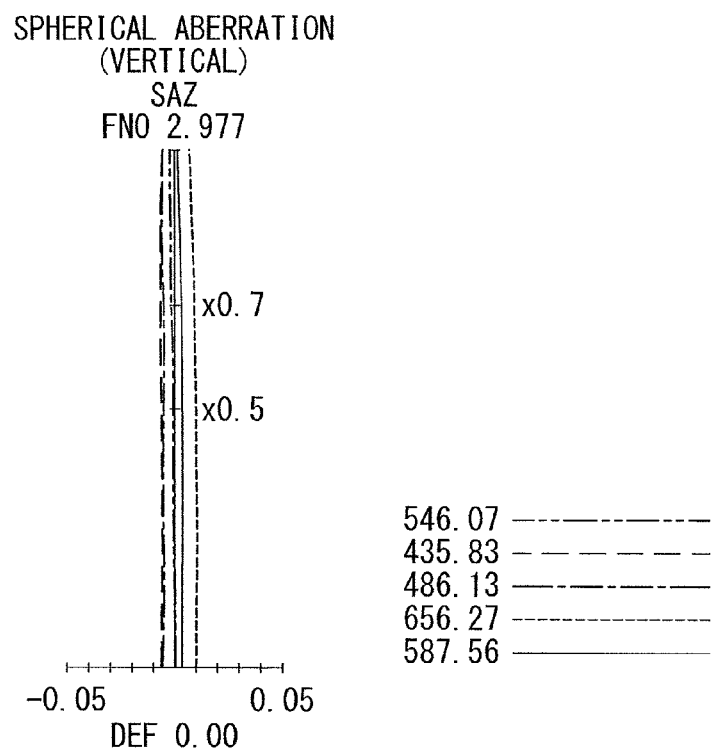
FIG. 11A is an aberration diagram of the endoscope objective optical system according to Example 5 of the present invention.
Figure 11B:
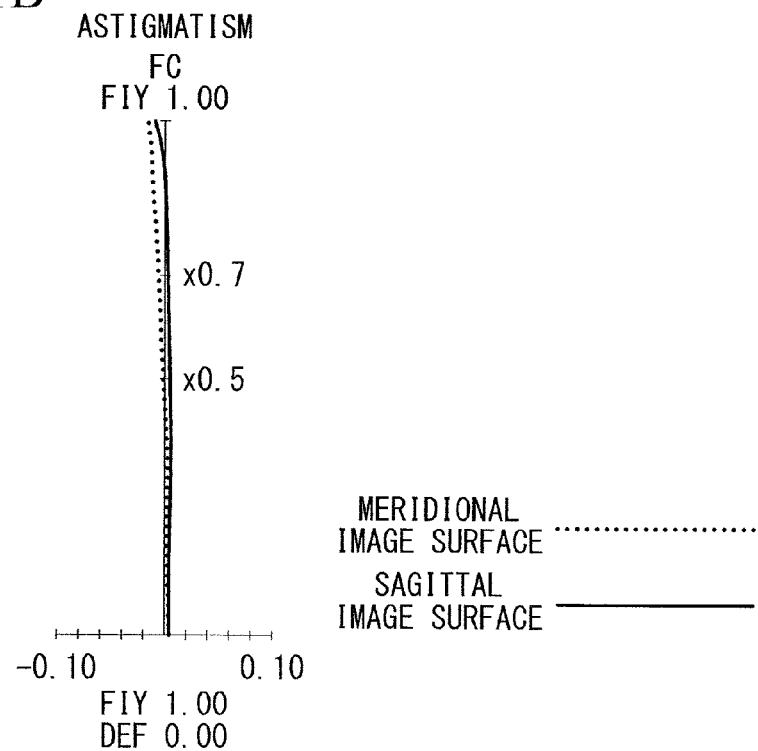
FIG. 11B is an aberration diagram of the endoscope objective optical system according to Example 5 of the present invention.
Figure 11C:
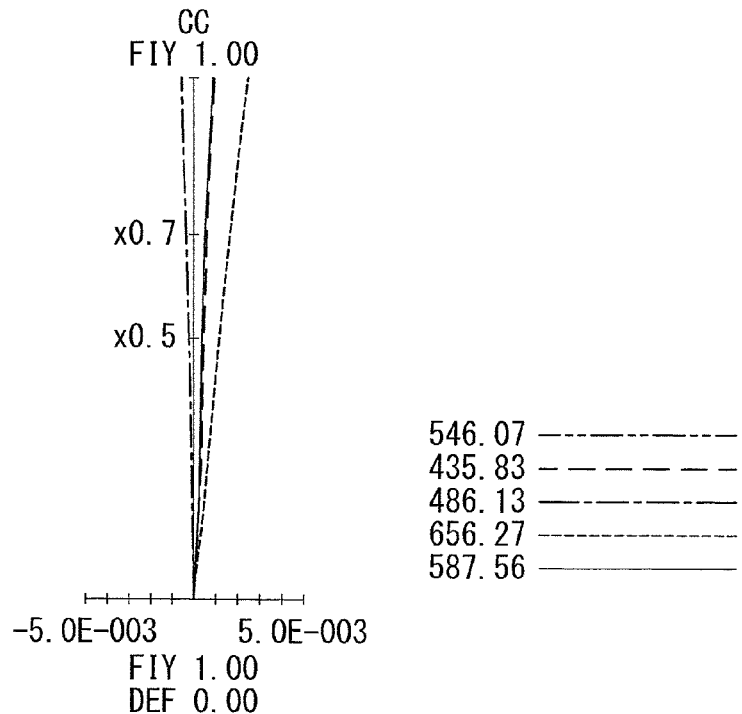
FIG. 11C is an aberration diagram of the endoscope objective optical system according to Example 5 of the present invention.
Figure 11D:
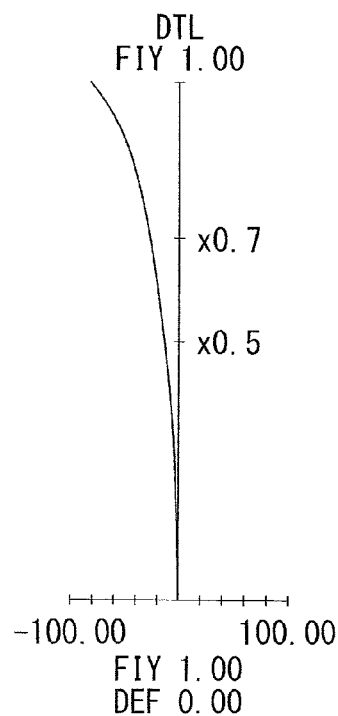
FIG. 11D is an aberration diagram of the endoscope objective optical system according to Example 5 of the present invention.

The overall configuration of the endoscope objective optical system according to Example 5 of the present invention is shown in FIG. 10, and the lens data thereof is shown below. Furthermore, aberration diagrams of the endoscope objective optical system according to this example are shown in FIGS. 11A to 11D.

| Lens Data | | | | |
|---|---|---|---|---|
| Surface Number | r | d | Ne | vd |
| object plane | ∞ | 21.6783 | | |
| 1 | ∞ | 0.5828 | 1.88815 | 40.76 |
| 2 | 1.3800 | 1.2587 | | |
| 3 | −3.9557 | 1.8182 | 1.85504 | 23.78 |
| 4 | −3.6853 | 0.4429 | | |
| 5 | ∞ | 0.9324 | 1.49357 | 75.00 |
| 6 | ∞ | 0.4196 | | |
| 7 (stop) | ∞ | 0.0699 | | |
| 8 | ∞ | 0.2331 | | |
| 9 | 8.3963 | 1.7716 | 1.83932 | 37.16 |
| 10 | −5.4522 | 0.2564 | | |
| 11 | 5.2308 | 1.8182 | 1.73234 | 54.68 |
| 12 | −1.9580 | 0.7459 | 1.93429 | 18.90 |
| 13 | −22.1492 | 0.8858 | | |
| 14 | 3.4615 | 1.1655 | 1.51825 | 64.14 |
| 15 | ∞ | 0.0233 | 1.51500 | 64.00 |
| 16 | ∞ | 0.8159 | 1.50700 | 63.26 |
| 17 | image-acquisition Surface | | | |

| Miscellaneous Data | |
|---|---|
| Focal Length | 0.967 |
| Fno | 2.987 |

Miscellaneous Data

| | |
|---|---|
| Half Angle of View | 81.4° |
| Image Height | 1.000 |
| Overall Length | 13.24 |

Example 6

Figure 12:
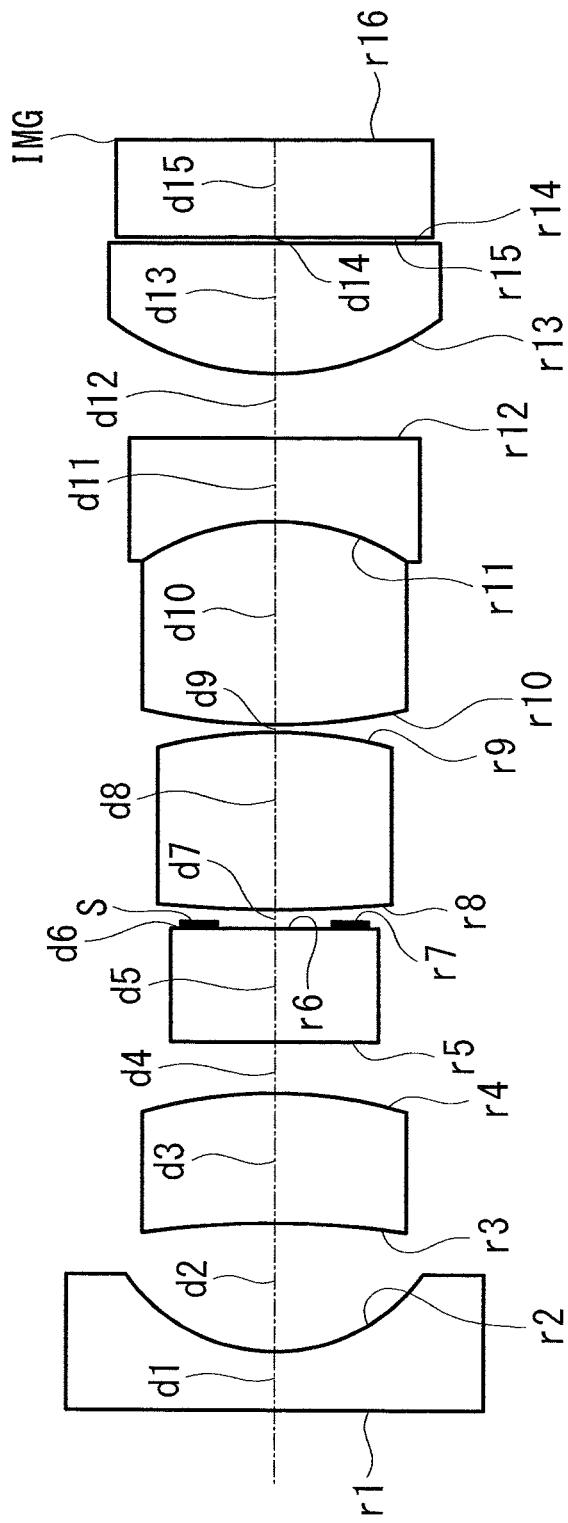
FIG. 12 is a cross-sectional view showing the overall configuration of an endoscope objective optical system according to Example 6 of the present invention.
Figure 13A:
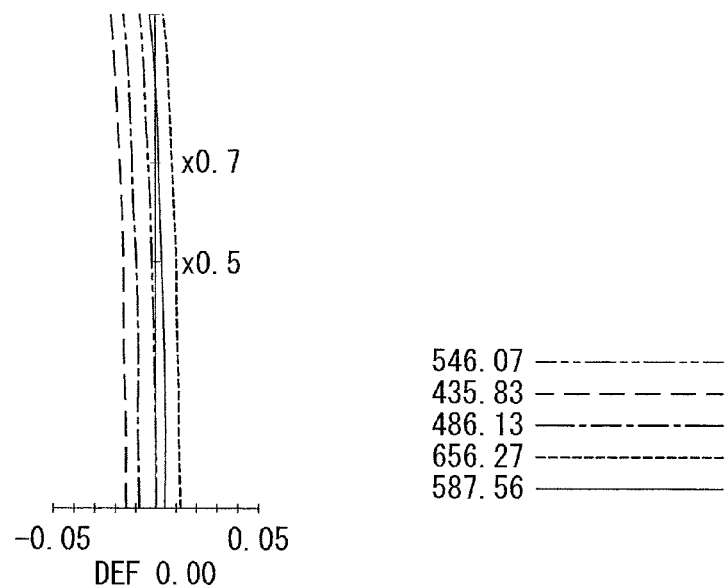
FIG. 13A is an aberration diagram of the endoscope objective optical system according to Example 6 of the present invention.
Figure 13B:
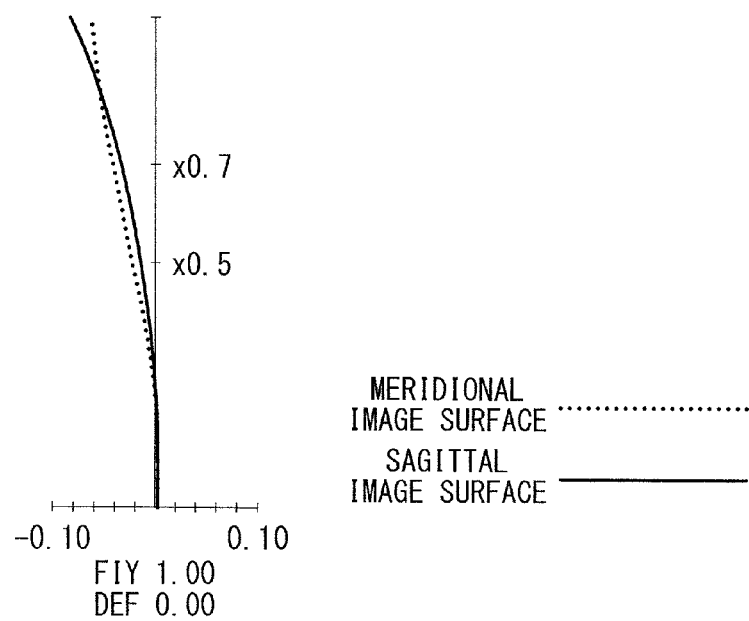
FIG. 13B is an aberration diagram of the endoscope objective optical system according to Example 6 of the present invention.
Figure 13C:
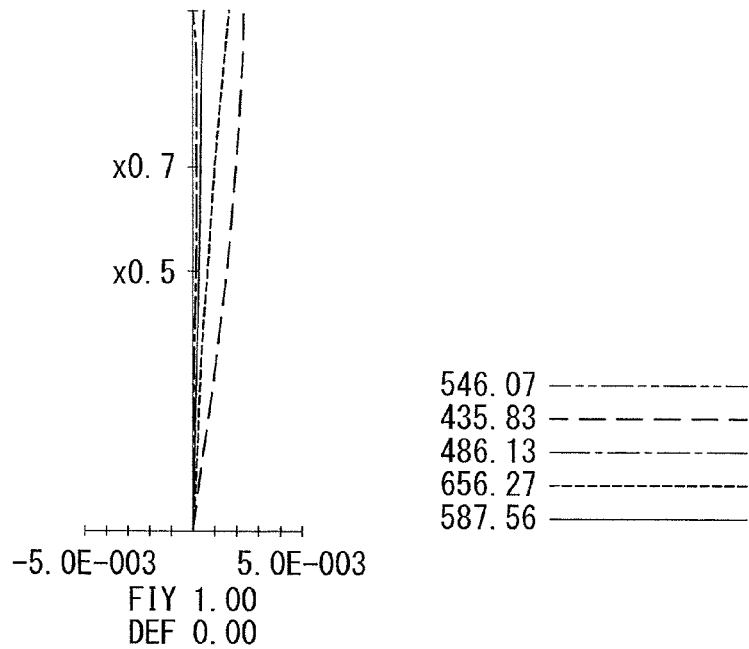
FIG. 13C is an aberration diagram of the endoscope objective optical system according to Example 6 of the present invention.
Figure 13D:
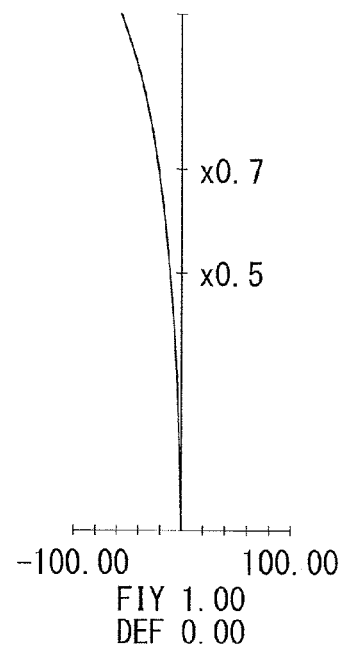
FIG. 13D is an aberration diagram of the endoscope objective optical system according to Example 6 of the present invention.

The overall configuration of the endoscope objective optical system according to Example 6 of the present invention is shown in FIG. 12, and the lens data thereof is shown below. Furthermore, aberration diagrams of the endoscope objective optical system according to this example are shown in FIGS. 13A to 13D.

Lens Data

| Surface Number | r | d | Ne | vd |
|---|---|---|---|---|
| object plane | ∞ | 26.7261 | | |
| 1 | ∞ | 0.4454 | 1.88815 | 40.76 |
| 2 | 1.3671 | 0.9914 | | |
| 3 | −8.8487 | 1.0115 | 1.93429 | 18.90 |
| 4 | −3.9093 | 0.3803 | | |
| 5 | ∞ | | | |
| 6 (stop) | ∞ | 0.0668 | | |
| 7 | ∞ | 0.0668 | | |
| 8 | 9.4083 | 1.3763 | 1.88815 | 40.76 |
| 9 | −3.5512 | 0.0668 | | |
| 10 | 4.8604 | 1.5506 | 1.69979 | 55.53 |
| 11 | −1.8438 | 0.6561 | 1.93429 | 18.90 |
| 12 | ∞ | 0.5025 | | |
| 13 | 2.1158 | 1.0022 | 1.51825 | 64.14 |
| 14 | ∞ | 0.0223 | 1.51500 | 64.00 |
| 15 | ∞ | 0.7795 | 1.50700 | 63.26 |
| 16 | image acquisition Surface | | | |

Miscellaneous Data

| | |
|---|---|
| Focal Length | 1.061 |
| Fno | 3.020 |
| Half Angle of View | 65.1° |
| Image Height | 1.000 |
| Overall Length | 9.81 |

Example 7

Figure 14:
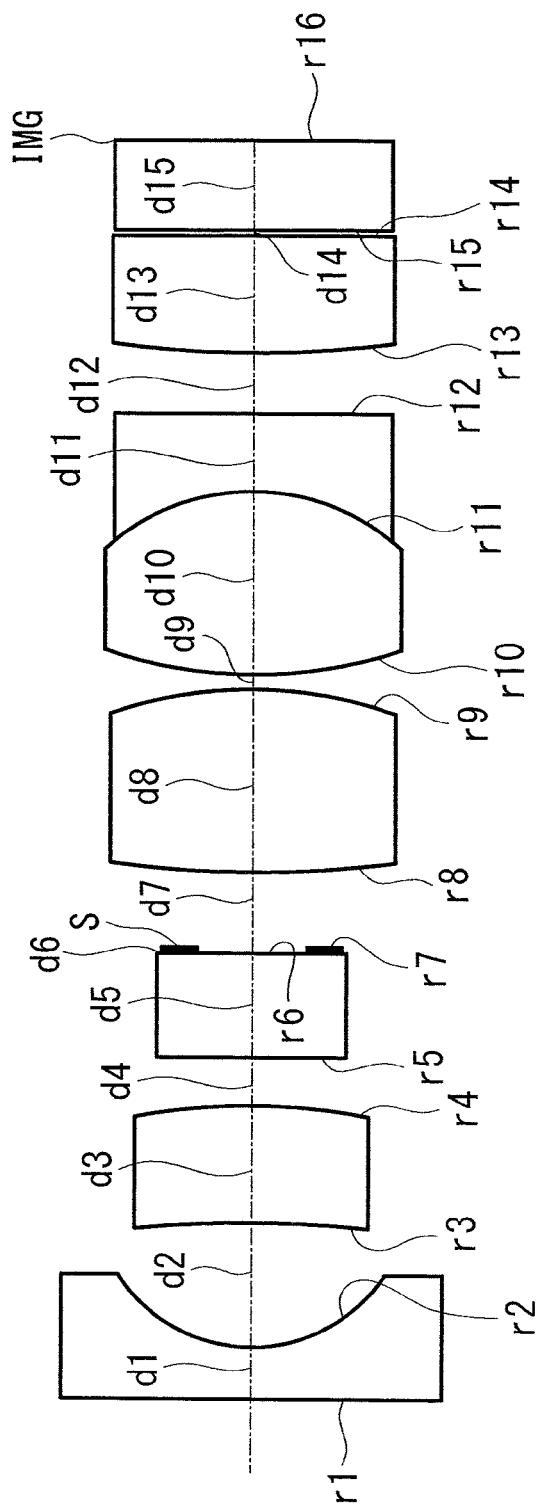
FIG. 14 is a cross-sectional view showing the overall configuration of an endoscope objective optical system according to Example 7 of the present invention.
Figure 15A:
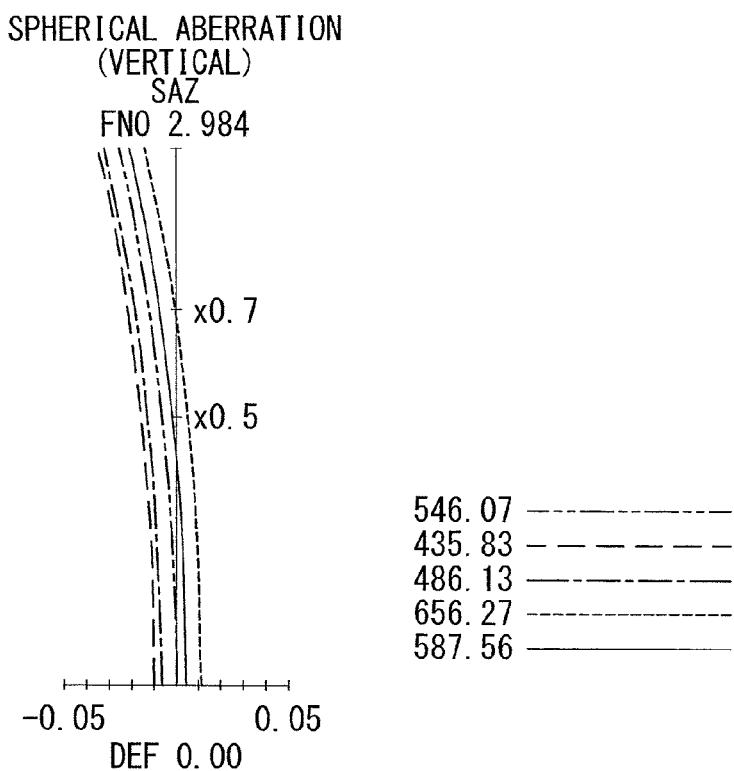
FIG. 15A is an aberration diagram of the endoscope objective optical system according to Example 7 of the present invention.
Figure 15B:
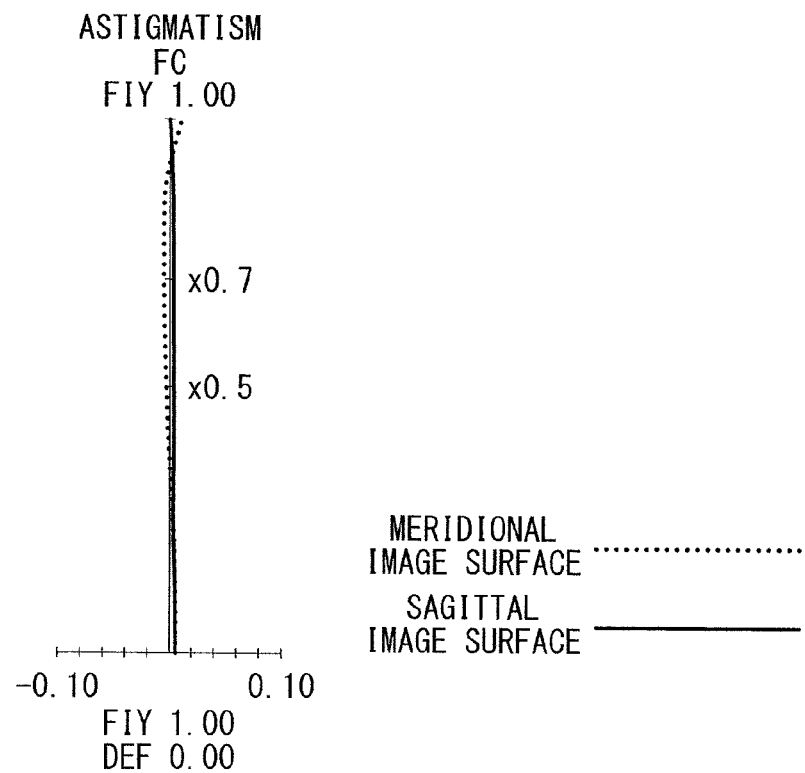
FIG. 15B is an aberration diagram of the endoscope objective optical system according to Example 7 of the present invention.
Figure 15C:
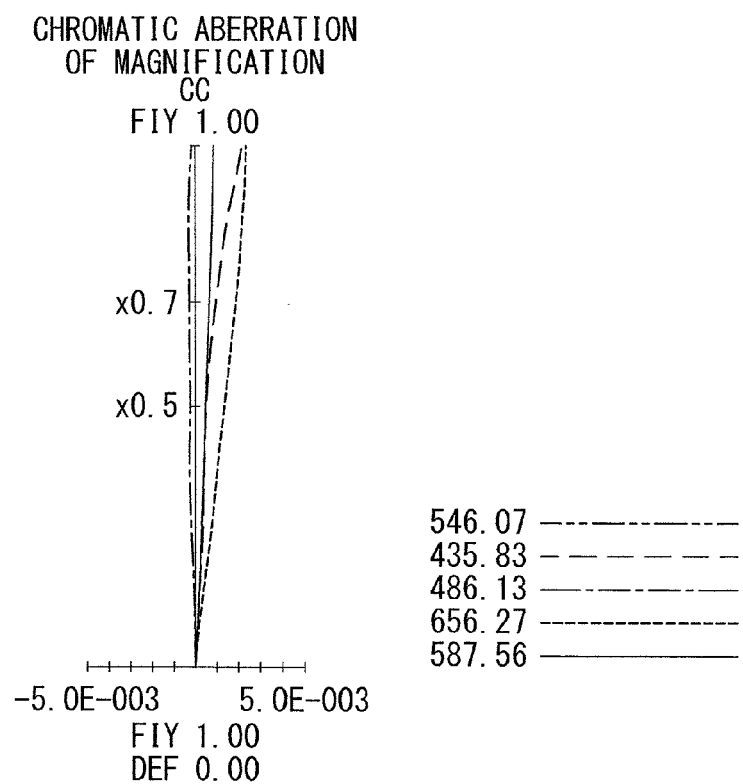
FIG. 15C is an aberration diagram of the endoscope objective optical system according to Example 7 of the present invention.
Figure 15D:
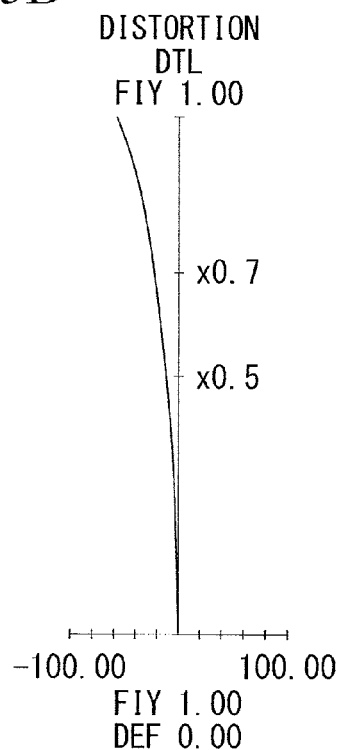
FIG. 15D is an aberration diagram of the endoscope objective optical system according to Example 7 of the present invention.

The overall configuration of the endoscope objective optical system according to Example 7 of the present invention is shown in FIG. 14, and the lens data thereof is shown below. Furthermore, aberration diagrams of the endoscope objective optical system according to this example are shown in FIGS. 15A to 15D.

Lens Data

| Surface Number | r | d | Ne | vd |
|---|---|---|---|---|
| object plane | ∞ | 26.7261 | | |
| 1 | ∞ | 0.4454 | 1.88815 | 40.76 |
| 2 | 1.3403 | 1.0420 | | |
| 3 | −11.3355 | 0.9880 | 1.93429 | 18.90 |
| 4 | −5.3538 | 0.3946 | | |
| 5 | ∞ | 0.8909 | 1.51500 | 75.00 |
| 6 (stop) | ∞ | 0.0668 | | |
| 7 | ∞ | 0.6312 | | |
| 8 | 9.7005 | 1.5363 | 1.88815 | 40.76 |
| 9 | −3.5452 | 0.1173 | | |
| 10 | 3.5940 | 1.5409 | 1.69979 | 55.53 |
| 11 | −1.8859 | 0.6621 | 1.93429 | 18.90 |
| 12 | ∞ | 0.5209 | | |
| 13 | 11.1359 | 1.0022 | 1.51825 | 64.14 |
| 14 | ∞ | 0.0223 | 1.51500 | 64.00 |
| 15 | ∞ | 0.7795 | 1.50700 | 63.26 |
| 16 | image-acquisition Surface | | | |

Miscellaneous Data

| | |
|---|---|
| Focal Length | 1.049 |
| Fno | 3.001 |
| Half Angle of View | 66.4° |
| Image Height | 1.000 |
| Overall Length | 10.64 |

Example 8

Figure 16:
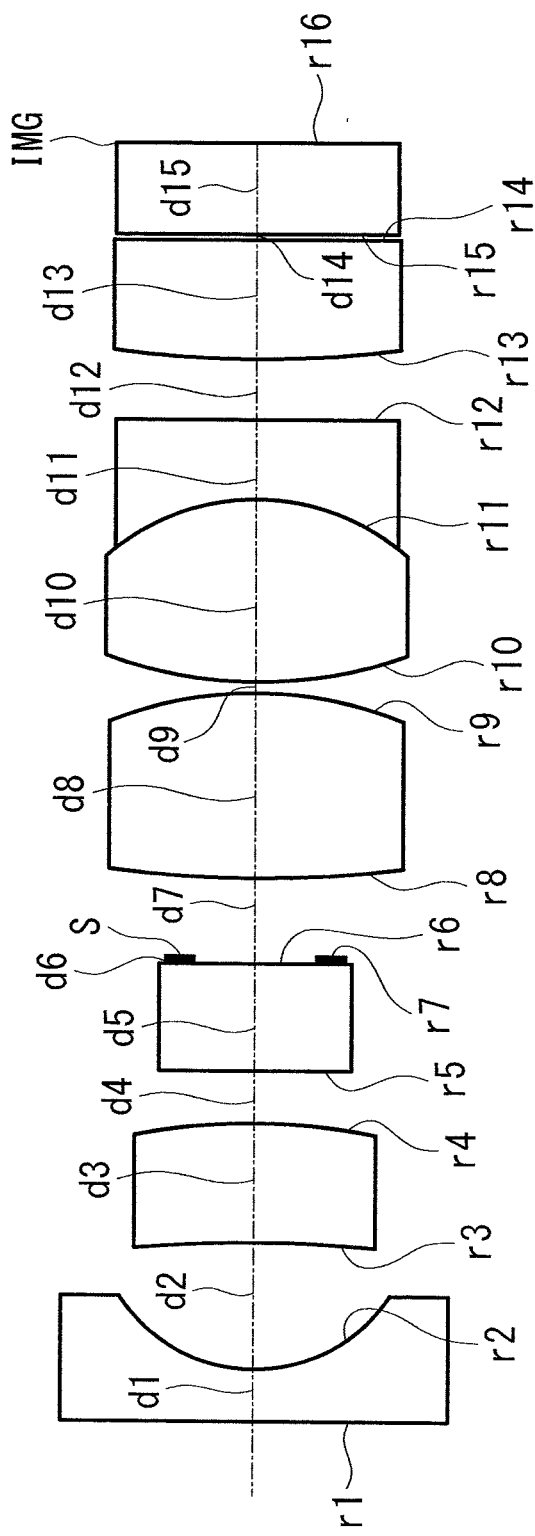
FIG. 16 is a cross-sectional view showing the overall configuration of an endoscope objective optical system according to Example 8 of the present invention.
Figure 17A:
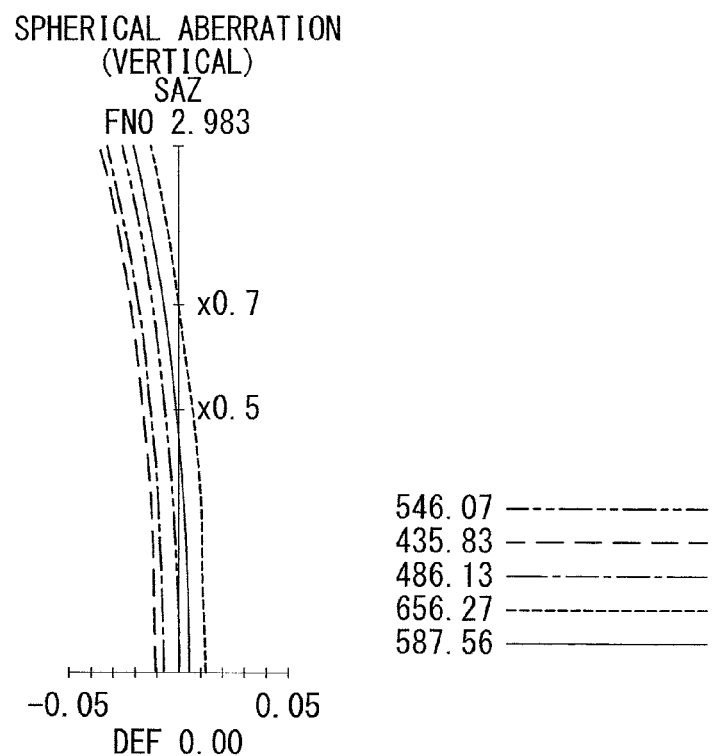
FIG. 17A is an aberration diagram of the endoscope objective optical system according to Example 8 of the present invention.
Figure 17B:
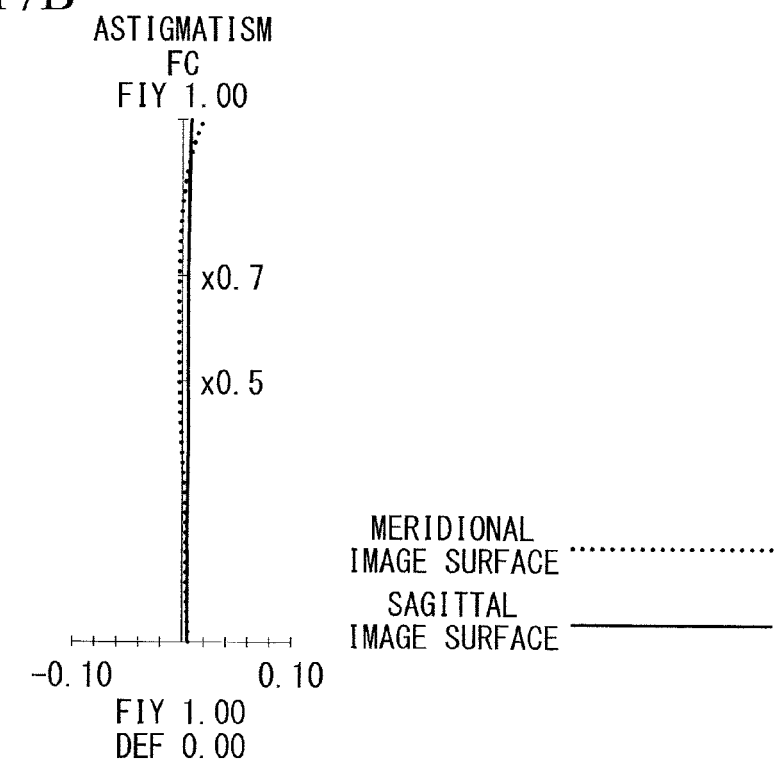
FIG. 17B is an aberration diagram of the endoscope objective optical system according to Example 8 of the present invention.
Figure 17C:
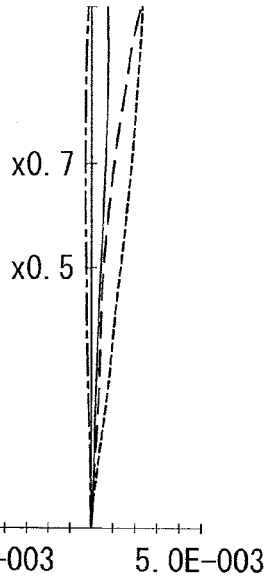
FIG. 17C is an aberration diagram of the endoscope objective optical system according to Example 8 of the present invention.
Figure 17D:
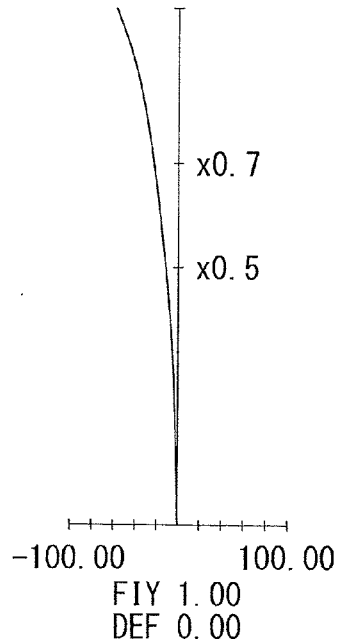
FIG. 17D is an aberration diagram of the endoscope objective optical system according to Example 8 of the present invention.

The overall configuration of the endoscope objective optical system according to Example 8 of the present invention is shown in FIG. 16, and the lens data thereof is shown below. Furthermore, aberration diagrams of the endoscope objective optical system according to this example are shown in FIGS. 17A to 17D.

Lens Data

| Surface Number | r | d | Ne | vd |
|---|---|---|---|---|
| object plane | ∞ | 26.7261 | | |
| 1 | ∞ | 0.4454 | 1.88815 | 40.76 |
| 2 | 1.3437 | 1.0364 | | |
| 3 | −11.4435 | 0.9802 | 1.93429 | 18.90 |
| 4 | −5.2698 | 0.4539 | | |
| 5 | ∞ | 0.8909 | 1.51500 | 75.00 |
| 6 (stop) | ∞ | 0.0668 | | |
| 7 | ∞ | 0.6343 | | |
| 8 | 9.7252 | 1.5315 | 1.88815 | 40.76 |
| 9 | −3.5438 | 0.0978 | | |
| 10 | 3.5342 | 1.5343 | 1.69979 | 55.53 |
| 11 | −1.8850 | 0.6595 | 1.93429 | 18.90 |
| 12 | ∞ | 0.5155 | | |
| 13 | 22.2717 | 1.0022 | 1.51825 | 64.14 |
| 14 | ∞ | 0.0223 | 1.51500 | 64.00 |
| 15 | ∞ | 0.7795 | 1.50700 | 63.26 |
| 16 | image-acquisition Surface | | | |

Miscellaneous Data

| | |
|---|---|
| Focal Length | 1.058 |
| Fno | 3.003 |

-continued

| Miscellaneous Data | |
|---|---|
| Half Angie of View | 65.4° |
| Image Height | 1.000 |
| Overall Length | 10.65 |

Although in the above-described examples, the configurations in which the sixth lens and the cover glass of the image-acquisition element are joined have been described, there is no problem with a configuration in which they are separated.

Values related to Conditional Expressions (1) to (10) in the endoscope objective optical systems according to Examples 1 to 8 are shown in Table 1.

TABLE 1

| Conditional Expression | Example 1 | Example 2 | Example 3 | Example 4 | Example 5 | Example 6 | Example 7 | Example 8 |
|---|---|---|---|---|---|---|---|---|
| (1) | 16.35 | 13.84 | 19.98 | 13.35 | 16.65 | 8.30 | 58.16 | 118.76 |
| (2) | 2.23 | 2.36 | 2.33 | 2.42 | 2.33 | 4.65 | 1.27 | 1.13 |
| (3) | −0.532 | −0.592 | −0.573 | −0.572 | −0.566 | −0.871 | −0.169 | −0.085 |
| (4) | 2.609 | 2.723 | 2.546 | 2.589 | 3.258 | 2.285 | 2.632 | 2.621 |
| (5) | −0.223 | −0.237 | −0.233 | −0.242 | −0.233 | −0.377 | −0.070 | −0.035 |
| (6) | 0.00457 | 0.00527 | 0.00484 | 0.00525 | 0.00887 | 0.00631 | 0.00119 | 0.00058 |
| (7) | −0.94 | −0.75 | −1.00 | −0.71 | −0.88 | −1.33 | −1.02 | −1.04 |
| (8) | 0.099 | 0.108 | 0.100 | 0.111 | 0.073 | 0.108 | 0.099 | 0.099 |
| (9) | 0.0943 | 0.0988 | 0.0965 | 0.1020 | 0.0755 | 0.1019 | 0.0940 | 0.0939 |
| (10) | 66.7 | 65.4 | 66.5 | 66.0 | 81.4 | 65.1 | 66.4 | 65.4 |

REFERENCE SIGNS LIST

1 endoscope objective optical system
G1 front group
G2 rear group
L1 first lens
L2 second lens
L3 third lens
L4 fourth lens
L5 fifth lens
L6 sixth lens
CL1 cemented lens
S aperture stop
P focus adjustment position
CG cover glass
IMG image plane

The invention claimed is:

1. An endoscope objective optical system comprising, in this order from an object side:
   a front group having negative refractive power as a whole;
   an aperture stop; and
   a rear group having positive refractive power as a whole, wherein
   the front group includes, in this order from the object side, a first lens, which is a single lens having negative refractive power, and a second lens, which is a single lens having positive refractive power,
   the rear group includes a third lens, which is a single lens having positive refractive power, a cemented lens formed of a fourth lens having positive refractive power and a fifth lens having negative refractive power, and a sixth lens having positive refractive power,
   an object-side surface of the first lens is a flat surface,
   the second lens has a meniscus shape,
   the sixth lens is joined to an image-acquisition element, and
   the endoscope objective optical system satisfies the following conditional expression:

$$4 < Fno \times F6/F1\_5 < 500 \quad (1)$$

where Fno is the effective F number of the endoscope objective optical system, F6 is the focal length of the sixth lens, and F1_5 is the composite focal length of the first to fifth lenses.

2. The endoscope objective optical system according to claim 1, satisfying the following conditional expression:

$$1.1 < SH\_R1R6 < 10 \quad (2)$$

where $SH\_R1R6 = |(R1R+R6L)/(R1R-R6L)|$, R1R is the radius of curvature of an image-side surface of the first lens, and R6L is the radius of curvature of an object-side surface of the sixth lens.

3. The endoscope objective optical system according to claim 1, satisfying the following conditional expression:

$$-1.5 < R4R/R6L < -0.01 \quad (3)$$

where R4R is the radius of curvature of an image-side surface of the fourth lens, and R6L is the radius of curvature of an object-side surface of the sixth lens.

4. The endoscope objective optical system according to claim 1, satisfying the following conditional expression:

$$2.2 < F23/FL < 4.0 \quad (4)$$

where F23 is the composite focal length of the second and third lenses, and FL is the composite focal length of the entire system.

5. The endoscope objective optical system according to claim 1, satisfying the following conditional expression:

$$-0.8 < F1/F6 < -0.01 \quad (5)$$

where F1 is the focal length of the first lens, and F6 is the focal length of the sixth lens.

6. The endoscope objective optical system according to claim 1, satisfying the following conditional expression:

$$0.0003 < P^2/(L \times F6) < 0.015 \quad (6)$$

where P is a distance between the fifth lens and the sixth lens, and L is the overall length of the endoscope objective optical system.

7. The endoscope objective optical system according to claim 1, satisfying the following conditional expression:

$$-2.0 < F12/F36 < -0.6 \quad (7)$$

where F12 is the composite focal length of the front group (first and second lenses), and F36 is the composite focal length of the rear group (from the third to sixth lenses).

8. The endoscope objective optical system according to claim 1, satisfying the following conditional expression:

$$0.05 < FL/L < 0.12 \quad (8)$$

9. The endoscope objective optical system according to claim 1, satisfying the following conditional expression:

$$0.06 < IH/L < 0.12 \quad (9)$$

where IH is the maximum image height.

10. The endoscope objective optical system according to claim 1, satisfying the following Conditional Expression (10):

$$\omega > 62° \quad (10)$$

where $\omega$ is the half angle of view.

* * * * *